(12) United States Patent
Lee et al.

(10) Patent No.: US 10,280,420 B2
(45) Date of Patent: May 7, 2019

(54) CANCER SPECIFIC-SPLICING RIBOZYME AND USE THEREOF

(71) Applicant: INDUSTRY-ACADEMIC COOPERATION FOUNDATION, DANKOOK UNIVERSITY, Gyeonggi-do (KR)

(72) Inventors: Seong Wook Lee, Seoul (KR); Ju Hyun Kim, Gyeonggi-do (KR); Jin Sook Jeong, Busan (KR); Sang Young Han, Busan (KR)

(73) Assignee: RZNOMICS INC., Gyeonggdi-Do (KR)

( * ) Notice: Subject to any disclaimer, the term of this patent is extended or adjusted under 35 U.S.C. 154(b) by 0 days.

(21) Appl. No.: 15/515,266

(22) PCT Filed: Jul. 23, 2015

(86) PCT No.: PCT/KR2015/007694
§ 371 (c)(1),
(2) Date: Jun. 2, 2017

(87) PCT Pub. No.: WO2016/052851
PCT Pub. Date: Apr. 7, 2016

(65) Prior Publication Data
US 2018/0187188 A1 Jul. 5, 2018

(30) Foreign Application Priority Data

Sep. 29, 2014 (KR) .................. 10-2014-0130286
Dec. 22, 2014 (KR) .................. 10-2014-0185976

(51) Int. Cl.
| | |
|---|---|
| A61K 48/00 | (2006.01) |
| C07H 21/02 | (2006.01) |
| C07H 21/04 | (2006.01) |
| C12N 15/113 | (2010.01) |
| A61K 38/43 | (2006.01) |
| A61K 31/713 | (2006.01) |
| C12N 15/85 | (2006.01) |
| C12N 15/86 | (2006.01) |
| C07K 14/47 | (2006.01) |
| C12N 9/22 | (2006.01) |
| C12N 15/63 | (2006.01) |
| C12N 15/79 | (2006.01) |
| A61K 38/00 | (2006.01) |

(52) U.S. Cl.
CPC .......... *C12N 15/113* (2013.01); *A61K 31/713* (2013.01); *A61K 38/43* (2013.01); *A61K 48/0058* (2013.01); *A61K 48/0066* (2013.01); *C07K 14/4705* (2013.01); *C12N 9/22* (2013.01); *C12N 15/1135* (2013.01); *C12N 15/63* (2013.01); *C12N 15/79* (2013.01); *C12N 15/85* (2013.01); *C12N 15/86* (2013.01); *A61K 38/00* (2013.01); *C07K 2319/01* (2013.01); *C07K 2319/33* (2013.01); *C07K 2319/61* (2013.01); *C12N 2310/113* (2013.01); *C12N 2310/12* (2013.01); *C12N 2310/124* (2013.01); *C12N 2310/128* (2013.01); *C12N 2330/51* (2013.01); *C12N 2710/10343* (2013.01); *C12N 2830/008* (2013.01); *C12N 2830/42* (2013.01); *C12N 2830/48* (2013.01)

(58) Field of Classification Search
CPC ...................... C12N 15/113; C12N 2310/14
See application file for complete search history.

(56) References Cited

FOREIGN PATENT DOCUMENTS

KR    1014788690000    6/2015

OTHER PUBLICATIONS

Hong et al., In Vivo Reprogramming of hTERT by Trans-splicing Ribozyme to Target Tumor Cells, The American Society of Gene Therapy, vol. 16, No. 1, 74-80, Jan. 2008.
Jeong et al., "Antitumor Effects of Systemically Delivered Adenovirus Harboring Trans-Splicing Ribozyme in Intrahepatic Colon Cancer Mouse Model", Clinical Cancer Research 2008; 14(1), Jan. 1, 2008.
Kim et al., "Image-aided Suicide Gene Therapy Utilizing Multi-functional hTERT-targeting Adenovirus for Clinical Translation in Hepatocellular Carcinoma", Thernaostics 2015, vol. 6, Issue 3, pp. 357368.
Kwon et al., "Intracellular efficacy of tumor-targeting group I intro-based trans-splicing ribozyme", The Journal of Gene Medicine, J Gene Med 2011; 13: 89-100.

(Continued)

*Primary Examiner* — Amy H Bowman
(74) *Attorney, Agent, or Firm* — Workman Nydegger

(57) ABSTRACT

The present invention relates to a recombination vector, a transformation cell into which the recombinant vector is introduced, a ribozyme expressed from the recombination vector, a prophylactic or therapeutic composition for liver cancer comprising the recombination vector and the ribozyme, and a therapeutic method for liver cancer using the composition, said recombination vector comprising: a tissue-specific promoter; and a ribozyme-target gene expression cassette comprising a trans-splicing ribozyme targeting a cancer-specific gene and a target gene connected to the 3' exon of the ribozyme, wherein a splicing donor/splicing acceptor sequence (SD/SA sequence) is connected to the 5' end of the ribozyme-target gene expression cassette, woodchuck hepatitis virus posttranscriptional regulatory element (WPRE) is connected to the 3' end of the ribozyme-target gene expression cassette, and a nucleic acid sequence recognizing a micro RNA-122a (microRNA-122a, miR-122a) is further connected to the 3' end of the WPRE.

9 Claims, 9 Drawing Sheets
Specification includes a Sequence Listing.

(56) References Cited

OTHER PUBLICATIONS

Kwon et al., "Specific Regression of Human Cancer Cells by Ribozyme-Mediated Targeted Replacement of Tumor-Specific Transcript", Molecular Therapy, vol. 12, No. 5, Nov. 2005, pp. 824-834.
Song et al., "Cancer-selective induction of cytotoxicity by tissue-specific expression of targeted trans-splicing ribozyme", FEBS Letters 580 (2006) 5033-5043.
Song et al., "Validation of tissue-specific promoter-driven tumor-targeting trans-splicing ribozyme system as a multifunctional cancer gene therapy device in vivo", Cancer Gene Therapy (2006, 16, 113-125.
Won et al., "Targeted anticancer effect through microRNA-181a regulated tumor-specific hTERT replacement", Cancer Letters 356 (2015), 918-928.
Database GenBank Aug. 2, 1993 (Aug. 2, 1993), "Herpes simplex virus type 1 thymidine kinase and 3KBL genes", Database accession No. J02224.1.
Jiyoung Im, "Studies on the improvement of efficacy of trans-splicing ribozyme for cancer therapy based on group I intron of Tetrahymena thermophila", Dept of Molecular Biology, Graduate School of Molecular Biology, Dankook University, 2012.
Kim et al., "Targeting Regression of Hepatocellular Carcinoma by Cancer-Specific RNA Replacement through MicroRNA Regulation", Scientific Reports, 5:12315, Jul. 20, 2015.
Jeong, Jin Sook, et al.: "Highly specific and effective HCC gene therapy based on cancer-specific RNA Replacement via liver-specific microRNA regulation in mouse model.", HEPATHOLOGY, vol. 56, No. Suppl.1, A1266, Oct. 1, 2012 (Oct. 1, 2012), pp. 793A, XP002779800, ISSN: 0270-9139.
Kim Ju-Hyun et al: "Anti-Cancer Approach Through MicroRNA-Regulated RNA Replacement", Nucleic Acid Therapeu, Mary Ann Liebert, Inc. Publishers, US, vol. 21, No. 5, Sep. 8, 2011 (Sep. 8, 2011), pp. A17, XP009183471, ISSN: 2159-3337.
Jeong Jin Sook et al: "In vivo HCC Gene therapy targeting by trans-splicing ribozyme and liver specific promoter with augumented safety", International Journal of Molecular Medicine, vol. 32, No. Suppl. 1, 2013, & 18th World Congress on Advances in Oncology / 16th International Symposium on Molecular Medicine; Crete, Greece; Oct. 10-12, 2013, pp. S12, XP002779801.
Xinping Fu et al: "Construction of an Oncolytic Herpes Simplex Virus That Precisely Targets Hepatocellular Carcinoma Cells", Molecular Therapy : The Journal of the American Society of Gene Therapy, vol. 20, No. 2, Feb. 1, 2012 (Feb. 1, 2012), US, pp. 339-346, XP055465038, ISSN: 1525-0016, DOI: 10.1038/mt.2011.265.
Won et al: "Targeted retardation of hepatocarcinoma cells by specific replacement of alpha-fetoprotein RNA", Journal of Biotechnology, Elsevier, Amsterdam, NL, vol. 129, No. 4, Apr. 19, 2007 (Apr. 19, 2007), pp. 614-619, XP022034272, ISSN: 0168-1656, DOI: 10.1016/J.JBIOTEC.2007.02.004.
Kim Ju-Hyun et al: "Development of cancer gene therapy based on cancer-specific RNA replacement through microRNA regulation", Human Gene Therapy, vol. 25, No. 11, Nov. 2014 (Nov. 14, 2014), & ESGCT and NVGCT Collaborative Congress; The Hague, Netherlands; Oct. 23-26, 2014, pp. A80-A81, XP002779803.
Jeong Jin-Sook et al: "Efficient and Safe HCC-specific Gene Therapy and Its Possible Role of Immunogenic Cell Death via Adenovirus Harboring mTERT-targeting Trans-splicing Ribozyme, Liver-specific Promoter and MicroRNA Regulation in Immunocompetent Mouse", HEPATOLOGY, vol. 60, No. Suppl. 1, Sp. Iss. SI, 2014, & 65th Annual Meeting of the American-Association-for-the-Study-of-Liver-Diseases; Boston, MA, USA; Nov. 7-11, 2014, pp. 827A, XP002779802.

```
                              SEQUENCE LISTING

<160> NUMBER OF SEQ ID NOS: 18

<210> SEQ ID NO 1
<211> LENGTH: 416
<212> TYPE: DNA
<213> ORGANISM: Artificial Sequence
<220> FEATURE:
<223> OTHER INFORMATION: PEPCK enhancer

<400> SEQUENCE: 1
ctcgaatctg tcacacgtct tagtaagcag agtcacagag tttctgtcac atcatcctcc      60
tgcctacagg gaagtaggcc atgtccctgc cccctactct gagcccagct gtgggagcca    120
gccctgccca atgggctctc tctgattggc ttctcactca cttctaaact ccagtgagca    180
acttctctcg gctcgttcaa ttggcgtgaa ggtctgtgtc ttgcagagaa ggttcttcac    240
aactgggata aaggtctcgc tgctcaagtg tagcccagta gaactgccaa gccccttccc    300
ctcctctccc tagactcttg gatgcaagaa gaatccaggc agctccaagg gtgattgtgt    360
ccaacctaga atgtcttgaa aaagacatta aggggactag agaagacagg ggatcc        416

<210> SEQ ID NO 2
<211> LENGTH: 227
<212> TYPE: DNA
<213> ORGANISM: Artificial Sequence
<220> FEATURE:
<223> OTHER INFORMATION: PEPCK promoter

<400> SEQUENCE: 2
aaagtttatt gtgttaggtc agttccaaac cgtgctgacc atggctatga tccaaaggcc     60 ggcccttac gtcagaggcg agcctccagg tccagctgag gggcagggct gtcctccctt    120
ctgtatacta tttaaagcga ggagggctag ctaccaagca cggttggcct tccctctggg    180
aacacaccct tggccaacag gggaaatccg gcgagacgct ctgagat                 227

<210> SEQ ID NO 3
<211> LENGTH: 172
<212> TYPE: DNA
<213> ORGANISM: Artificial Sequence
<220> FEATURE:
<223> OTHER INFORMATION: SD/SA

<400> SEQUENCE: 3
accagaaagt taactggtaa gtttagtctt tttgtctttt atttcaggtc ccggatccgg      60
tggtggtgca aatcaaagaa ctgctcctca gtggatgttg cctttacttc taggcctgta   120
cggaagtgtt acttctgctc taaaagctgc ggaattgtac ccaggcctag gc            172

<210> SEQ ID NO 4
<211> LENGTH: 325
<212> TYPE: DNA
<213> ORGANISM: Artificial Sequence
<220> FEATURE:
<223> OTHER INFORMATION: AS300

<400> SEQUENCE: 4
aaggccagca cgttcttcgc gccgcgctcg cacagcctct gcagcactcg ggccaccagc     60
tccttcaggc aggacacctg gcggaaggag ggggcggcgg ggggcggccg tgcgtcccag   120
```

| | |
|---|---|
| ggcacgcaca ccaggcactg ggccaccagc gcgcggaaag ccgccgggtc cccgcgctgc | 180 |
| accagccgcc agccctgggg ccccaggcgc cgcacgaacg tggccagcgg cagcacctcg | 240 |
| cggtagtggc tgcgcagcag ggagcgcacg gctaggcagc ggggagcgcg cggcatcgcg | 300 |
| ggggtggccg gggccagggc ttccc | 325 |

```
<210> SEQ ID NO 5
<211> LENGTH: 401
<212> TYPE: DNA
<213> ORGANISM: Artificial Sequence
<220> FEATURE:
<223> OTHER INFORMATION: ribozyme

<400> SEQUENCE: 5
```

| | |
|---|---|
| cgttttgcgg caggaaaagt tatcaggcat gcacctggta gctagtcttt aaaccaatag | 60 |
| attgcatcgg tttaaaaggc aagaccgtca aattgcggga aaggggtcaa cagccgttca | 120 |
| gtaccaagtc tcaggggaaa ctttgagatg gccttgcaaa gggtatggta ataagctgac | 180 |
| ggacatggtc ctaaccacgc agccaagtcc taagtcaaca gatcttctgt tgatatggat | 240 |
| gcagttcaca gactaaatgt cggtcgggga agatgtattc ttctcataag atatagtcgg | 300 |
| acctctcctt aatgggagct agcggatgaa gtgatgcaac actggagccg ctgggaacta | 360 |
| atttgtatgc gaaagtatat tgattagttt tggagtactc g | 401 |

```
<210> SEQ ID NO 6
<211> LENGTH: 1144
<212> TYPE: DNA
<213> ORGANISM: Artificial Sequence
<220> FEATURE:
<223> OTHER INFORMATION: HSV TK

<400> SEQUENCE: 6
```

| | |
|---|---|
| cgaaaacgcc caccatggct tcgtaccect gccatcaaca cgcgtctgcg ttcgaccagg | 60 |
| ctgcgcgttc tcgcggccat agcaaccgac gtacggcgtt gcgccctccc ggcagcaaga | 120 |
| agccacggaa gtccgcctgg agcagaaaat gcccacgcta ctgcgggttt atatagacgg | 180 |
| tcctcacggg atggggaaaa ccaccaccac gcaactgctg gtggccctgg ttcgcgcga | 240 |
| cgatatcgtc tacgtacccg agccgatgac ttactggcag gtgctggggg cttccgagac | 300 |
| aatcgcgaac atctacacca cacaacaccg cctcgaccag ggtgagatat cggccgggga | 360 |
| cgcggcggtg gtaatgacaa cgcccagat aacaatgggc atgccttatg ccgtgaccga | 420 |
| cgccgttctg gctcctcata cggggggga ggctgggagc tcacatgccc cgcccccggc | 480 |
| cctcacccte atcttcgacc gccatcccat cgccgccctc ctgtgctacc cggccgcgcg | 540 |
| ataccttatg ggcagcatga ccccccaggc cgtgctggcg ttcgtggccc tcatcccgcc | 600 |
| gaccttgccc ggcacaaaca tcgtgttggg ggcccttccg gaggacagac acatcgaccg | 660 |
| cctggccaaa cgccagcgcc ccggcgagcg gcttgacctg gctatgctgg ccgcgattcg | 720 |
| ccgcgtttac gggctgcttg ccaatacggt gcggtatctg cagggcggcg ggtcgtggtg | 780 |
| ggaggattgg ggacagcttt cggggacggc cgtgccgccc cagggtgccg agccccagag | 840 |
| caacgcgggc ccacgacccc atatcgggga cacgttattt accctgtttc gggccccga | 900 |
| gttgctggcc cccaacggcg acctgtataa cgtgtttgcc tgggccttgg acgtcttggc | 960 |
| caaacgcctc cgtcccatgc acgtctttat cctggattac gaccaatcgc ccgccggctg | 1020 |
| ccgggacgcc ctgctgcaac ttacctccgg gatggtccag acccacgtca ccaccccagg | 1080 |
| ctccataccg acgatctgcg acctggcgcg cacgtttgcc cgggagatgg gggaggctaa | 1140 | ctga                                                                1144

<210> SEQ ID NO 7
<211> LENGTH: 589
<212> TYPE: DNA
<213> ORGANISM: Artificial Sequence
<220> FEATURE:
<223> OTHER INFORMATION: WPRE

<400> SEQUENCE: 7
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctcttta tgaggagttg   180
tggcccgttg tcaggcaacg tggcgtggtg tgcactgtgt ttgctgacgc aaccccact    240 ggttggggca ttgccaccac ctgtcagctc ctttccggga cttttgcttt cccctccct    300 attgccacgg cggaactcat cgccgcctgc cttgcccgct gctggacagg ggctcggctg   360
ttgggcactg acaattccgt ggtgttgtcg gggaaatcat cgtcctttcc ttggctgctc   420
gcctgtgttg ccacctggat tctgcgcggg acgtccttct gctacgtccc ttcggccctc   480
aatccagcgg accttccttc ccgcggcctg ctgccggctc tgcggcctct tccgcgtctt   540
cgccttcgcc ctcagacgag tcggatctcc ctttgggccg cctccccgc                589

<210> SEQ ID NO 8
<211> LENGTH: 16
<212> TYPE: DNA
<213> ORGANISM: Artificial Sequence
<220> FEATURE:
<223> OTHER INFORMATION: miR-122aT

<400> SEQUENCE: 8
acaaacacca ttgtca                                                    16

<210> SEQ ID NO 9
<211> LENGTH: 23
<212> TYPE: DNA
<213> ORGANISM: Artificial Sequence
<220> FEATURE:
<223> OTHER INFORMATION: mut miR-122aT

<400> SEQUENCE: 9
acaaacacca ttcctcacac tga                                            23

<210> SEQ ID NO 10
<211> LENGTH: 31
<212> TYPE: DNA
<213> ORGANISM: Artificial Sequence
<220> FEATURE:
<223> OTHER INFORMATION: forward primer for WPRE cloning

<400> SEQUENCE: 10
gcggccggcc aatcaacctc tggattacaa a                                   31

<210> SEQ ID NO 11
<211> LENGTH: 28
<212> TYPE: DNA
<213> ORGANISM: Artificial Sequence
<220> FEATURE:
<223> OTHER INFORMATION: reverse primer for WPRE cloning

<400> SEQUENCE: 11
gcggccggcc gcggggaggc ggcccaaa                                              28

<210> SEQ ID NO 12
<211> LENGTH: 64
<212> TYPE: DNA
<213> ORGANISM: Artificial Sequence
<220> FEATURE:
<223> OTHER INFORMATION: forward primer for miR122aT cloning

<400> SEQUENCE: 12
ataagaatgc ggccgcacaa acaccattgt cacactccac gatacaaaca ccattgtcac    60
actc                                                                64

<210> SEQ ID NO 13
<211> LENGTH: 65
<212> TYPE: DNA
<213> ORGANISM: Artificial Sequence
<220> FEATURE:
<223> OTHER INFORMATION: reverse primer for miR122aT cloning

<400> SEQUENCE: 13
ataagaatgc ggccgctgga gtgtgacaat ggtgtttgta tcgtggagtg tgacaatggt    60
gtttg                                                               65

<210> SEQ ID NO 14
<211> LENGTH: 64
<212> TYPE: DNA
<213> ORGANISM: Artificial Sequence
<220> FEATURE:
<223> OTHER INFORMATION: forward primer for (E)PRT-mut 122aT cloning

<400> SEQUENCE: 14
ataagaatgc ggccgcacaa acaccattcc tcacactgac gatacaaaca ccattcctca    60
cact                                                                64

<210> SEQ ID NO 15
<211> LENGTH: 65
<212> TYPE: DNA
<213> ORGANISM: Artificial Sequence
<220> FEATURE:
<223> OTHER INFORMATION: reverse primer for (E)PRT-mut 122aT cloning

<400> SEQUENCE: 15
ataagaatgc ggccgctcag tgtgaggaat ggtgtttgta tcgtcagtgt gaggaatggt    60
gtttg                                                               65

<210> SEQ ID NO 16
<211> LENGTH: 20
<212> TYPE: DNA
<213> ORGANISM: Artificial Sequence
<220> FEATURE:
<223> OTHER INFORMATION: TK specific binding forward primer

<400> SEQUENCE: 16
tgacttactg gcaggtgctg                                               20

<210> SEQ ID NO 17
<211> LENGTH: 21
<212> TYPE: DNA
<213> ORGANISM: Artificial Sequence
<220> FEATURE:
<223> OTHER INFORMATION: TK specific binding reverse primer

<400> SEQUENCE: 17
ccattgttat ctgggcgctt g                                                  21

<210> SEQ ID NO 18
<211> LENGTH: 4404
<212> TYPE: DNA
<213> ORGANISM: Artificial Sequence
<220> FEATURE:
<223> OTHER INFORMATION: PEPCK-SD/SA-rib-TK-WPRE-122aT(EPRT-122aT)

<400> SEQUENCE: 18

```
ctcgaatctg tcacacgtct tagtaagcag agtcacagag tttctgtcac atcatcctcc      60
tgcctacagg gaagtaggcc atgtccctgc ccctactct gagcccagct gtgggagcca     120
gccctgccca atgggctctc tctgattggc ttctcactca cttctaaact ccagtgagca    180
acttctctcg gctcgttcaa ttggcgtgaa ggtctgtgtc ttgcagagaa ggttcttcac    240
aactgggata aggtctcgc tgctcaagtg tagcccagta gaactgccaa gccccttccc     300
ctcctctccc tagactcttg gatgcaagaa gaatccaggc agctccaagg gtgattgtgt    360
ccaacctaga atgtcttgaa aaagacatta aggggactag agaagacagg ggatccaacg    420
gttctctgca gcccagcctg actgacatgt aactcttctg gttctcacca gccagctgga    480
cctgcttagt attctttctg cctcagtttc ccagcctgta cccagggctg tcatagttcc    540
atttcaggca gtagtaatga atgagctgac ataaaacatt tagagcaggg gtcagtatgt    600
atatagagtg attattctat atcaggcatt gcctcctcgg aatgaagctt acaatcaccc    660
ctccctctgc agttcatctt gggtggcca gaggatccag cagacaccta gtggggtaac      720
acacccccagc caactcggct gttgcagact ttgtctagaa gtttcacgtc tcagagctga    780
attcccttct catgaccttt ggccgtggga gtgacacctc acagctgtgg tgttttgaca    840
accagcagcc actggcacac aaaatgtgca gccagcagca tatgaagtcc aagaggcgtc    900
ccggccagcc ctgtccttga ccccccacctg acaattaagg caagagccta tagtttgcat    960
cagcaacagt cacggtcaaa gtttagtcaa tcaaacgttg tgtaaggact caactatggc   1020
tgacacgggg gcctgaggcc tcccaacatt cattaacaac agcaagttca atcattatct   1080
ccccaaagtt tattgtgtta ggtcagttcc aaaccgtgct gaccatggct atgatccaaa   1140
ggccggcccc ttacgtcaga ggcgagcctc caggtccagc tgagggggcag ggctgtcctc  1200
ccttctgtat actatttaaa gcgaggaggg ctagctacca agcacggttg gccttccctc   1260
tgggaacaca cccttggcca acaggggaaa tccggcgaga cgctctgaga tcctgcgaga   1320
aggaggtgcg tcctgctgcc tgccccggca ctctggctcc ccagctcaag gttcaggcct   1380
tgccccaggc cgggcctctg ggtacctgag gtcttctccc gctctgtgcc cttctcctca   1440
cctggctgca atgagtgggg gagcacgggg cttctgcatg ctgaaggcac cccactcagc   1500
caggcccttc ttctcctcca ggtcccccac ggcccttcag atctgaactg aaaaaccaga   1560
aagttaactg gtaagtttag tcttttttgtc ttttattca ggtcccggat ccggtggtgg   1620
tgcaaatcaa agaactgctc ctcagtggat gttgccttta cttctaggcc tgtacggaag  1680
tgttacttct gctctaaaag ctgcggaatt gtacccaggc ctaggcttttt gcaaaaagct   1740
tcgaatcgcg aaaggccagc acgttcttcg cgccgcgctc gcacagcctc tgcagcactc   1800
gggccaccag ctccttcagg caggacacct ggcggaagga gggggcggcg ggggcggcc   1860
gtgcgtccca gggcacgcac accaggcact gggccaccag cgcgcggaaa gccgccgggt   1920
ccccgcgctg caccagccgc cagccctggg gcccaggcg ccgcacgaac gtggccagcg    1980
```

```
gcagcacctc gcggtagtgg ctgcgcagca gggagcgcac ggctaggcag cggggagcgc    2040
gcggcatcgc gggggtggcc ggggccaggg cttcccaagc ttcgttttgc ggcaggaaaa    2100
gttatcaggc atgcacctgg tagctagtct ttaaaccaat agattgcatc ggtttaaaag    2160
gcaagaccgt caaattgcgg gaaagggggtc aacagccgtt cagtaccaag tctcagggga   2220
aactttgaga tggccttgca aagggtatgg taataagctg acggacatgg tcctaaccac    2280
gcagccaagt cctaagtcaa cagatcttct gttgatatgg atgcagttca cagactaaat    2340
gtcggtcggg aagatgtat tcttctcata agatatagtc ggacctctcc ttaatgggag     2400
ctagcggatg aagtgatgca acactggagc cgctgggaac taatttgtat gcgaaagtat    2460
attgattagt tttggagtac tcgcgaaaac gcccaccatg gcttcgtacc cctgccatca    2520
acacgcgtct gcgttcgacc aggctgcgcg ttctcgcggc catagcaacc gacgtacggc    2580
gttgcgccct cccggcagca agaagccacg gaagtccgcc tggagcagaa aatgcccacg    2640
ctactgcggg tttatataga cggtcctcac gggatgggga aaaccaccac cacgcaactg    2700
ctggtggccc tgggttcgcg cgacgatatc gtctacgtac ccgagccgat gacttactgg    2760
caggtgctgg gggcttccga gacaatcgcg aacatctaca ccacacaaca ccgcctcgac    2820
cagggtgaga tatcggccgg ggacgcggcg gtggtaatga caagcgccca gataacaatg    2880
ggcatgcctt atgccgtgac cgacgccgtt ctggctcctc atatcggggg ggaggctggg   2940
agctcacatg ccccgccccc ggccctcacc ctcatcttcg accgccatcc catcgccgcc    3000
ctcctgtgct acccggccgc gcgataccgtt atgggcagca tgaccccccca ggccgtgctg   3060 gcgttcgtgg ccctcatccc gccgaccttg cccggcacaa acatcgtgtt gggggccctt    3120
ccggaggaca gacacatcga ccgcctggcc aaacgccagc gccccggcga gcggcttgac    3180
ctggctatgc tggccgcgat tcgccgcgtt tacgggctgc ttgccaatac ggtgcggtat    3240
ctgcagggcg gcgggtcgtg gtgggaggat tggggacagc tttcggggac ggccgtgccg    3300
ccccagggtg ccgagcccca gagcaacgcg ggcccacgac cccatatcgg ggacacgtta    3360
tttaccctgt ttcgggcccc cgagttgctg gcccccaacg gcgacctgta taacgtgttt    3420
gcctgggcct tggacgtctt ggccaaacgc ctccgtccca tgcacgtctt tatcctggat    3480
tacgaccaat cgcccgccgg ctgccgggac gccctgctgc aacttacctc cgggatggtc    3540
cagacccacg tcaccacccc aggctccata ccgacgatct gcgacctggc gcgcacgttt    3600
gcccgggaga tgggggggagc taactgaagg ccggccaatc aacctctgga ttacaaaatt    3660
tgtgaaagat tgactggtat tcttaactat gttgctcctt ttacgctatg tggatacgct    3720
gctttaatgc ctttgtatca tgctattgct tcccgtatgg ctttcatttt ctcctccttg    3780
tataaatcct ggttgctgtc tctttatgag gagttgtggc ccgttgtcag gcaacgtggc    3840
gtggtgtgca ctgtgtttgc tgacgcaacc cccactggtt ggggcattgc caccacctgt    3900
cagctccttt ccgggacttt cgctttcccc ctccctattg ccacggcgga actcatcgcc    3960
gcctgccttg cccgctgctg acagggggct cggctgttgg gcactgacaa ttccgtggtg    4020
ttgtcgggga aatcatcgtc cttccttgg ctgctcgcct gtgttgccac ctggattctg    4080
cgcgggacgt ccttctgcta cgtcccttcg gccctcaatc cagcggacct tccttcccgc    4140
ggcctgctgc cggctctgcg gcctcttccg cgtcttcgcc ttcgccctca gacgagtcgg    4200
```

```
atctcccttt gggccgcctc cccgcgcggc cgcacaaaca ccattgtcac actccacgat    4260
acaaacacca ttgtcacact ccacgataca aacaccattg tcacactcca gcggccgcgg    4320
tggcatccct gtgaccoctc cccagtgcct ctcctggccc tggaagttgc cactccagtg    4380
cccaccagcc ttgtcctaat aaaa                                            4404
```

CANCER SPECIFIC-SPLICING RIBOZYME AND USE THEREOF

TECHNICAL FIELD

The present invention relates to a recombinant vector comprising: (i) a tissue-specific promoter; and (ii) a ribozyme-target gene expression cassette comprising a trans-splicing ribozyme targeting a cancer-specific gene and a target gene linked to the 3' exon of the ribozyme, wherein a splicing donor/splicing acceptor sequence (SD/SA sequence) is linked to the 5' end of the ribozyme-target gene expression cassette and a woodchuck hepatitis virus post-transcriptional regulatory element (WPRE) is linked to the 3' end of the ribozyme-target gene expression cassette, and wherein (iii) a nucleic acid sequence recognizing a micro RNA-122a (microRNA-122a, miR-122a) is further linked to the 3' end of the WPRE; a transformed cell into which the recombinant vector is introduced; a ribozyme expressed from the recombinant vector; a pharmaceutical composition for preventing or treating hepatocellular carcinoma, comprising the recombinant vector or the ribozyme; and a method for treating hepatocellular carcinoma using the composition.

BACKGROUND ART

Cancer is the leading cause of death in Korea, which can occur in all parts of the body and can also be caused by various factors such as environmental factors and genetic factors. There have been many studies to conquer cancer, but it is an incurable disease that has not yet been conquered. Existing therapies for cancer include surgery, chemotherapy, radiation therapy, etc, and the prognosis is improving with the advance of medicine, but there are many limitations that can adversely affect normal cells as well as cancer cells. In recent years, other therapies whose concept is different from these therapies have been studied and, among other things, gene therapies for effectively treating only cancer cells have been actively studied.

The term "gene therapy" refers to a method of treating inherited or acquired genetic abnormalities, which are difficult to treat by conventional methods, using genetic engineering methods. Specifically, gene therapy comprises administering genetic materials such as DNA and RNA into the human body to express therapeutic proteins or inhibit the expression of specific proteins in order to treat and prevent inherited or acquired genetic defects, viral diseases, or chronic diseases such as cancer or cardiovascular diseases. Gene therapy can fundamentally treat diseases by analyzing the causes of diseases on a genetic basis and thus is expected to treat incurable diseases and is also potential as an alternative to conventional therapeutic methods.

Moreover, cancer tissue-targeted therapy has been attempted in an effort to reduce side effects that occur because a number of target genes that can be used in gene therapy are also expressed in normal cells that undergo significant cell division (Fukuzawa et al., Cancer Res 64: 363-369, 2004). For this end, a method of using a tissue-specific promoter instead of CMV or RSV has been proposed, but this method has not been put to practical use due to its low therapeutic efficacy, despite the increased specificity increases.

In addition, studies have recently been conducted to develop a tissue-specific adenovirus for cancer therapy using factors other than the tissue-specific promoter, and as a typical example, a method of using a trans-splicing ribozyme, etc. has been developed.

Studies on the development of a tissue-specific adenovirus for cancer therapy using the trans-splicing ribozyme have demonstrated that the group I intron ribozyme from Tetrahymena thermophila can perform trans-splicing reactions to link two separate transcripts in vitro as well as in bacterial cells and human cells, and thus have attracted much attention.

Specifically, the trans-splicing ribozyme based on this group I intron can target a disease-related gene transcript or a specific RNA that is specifically expressed in diseased cells, causing reprogramming such that the RNA can be restored to a normal RNA or the transcript can be replaced with a new therapeutic gene transcript, and thus it is expected that the trans-splicing ribozyme can be a disease-specific and safe gene therapy technology. In addition, the trans-splicing ribozyme can remove disease-specific RNA and, at the same time, induce the expression of desired therapeutic gene product, thereby increasing the therapeutic effect.

In recent studies, a trans-splicing ribozyme that targets human telomerase reverse transcriptase (hTERT) capable of acting specifically on cancer tissue has been known, and thus attempts to develop cancer therapeutic agents using this trans-splicing ribozyme have been actively made. However, it exhibits high tissue specificity due to a combination with a tissue-specific promoter, but the expression efficiency is low, and thus the disadvantage of low therapeutic efficiency has not yet been overcome. Moreover, in the case of treatment targeting hTERT, it shows telomerase activity also in normal cells such as stem cells, hematopoietic stem cells, germ cells, and regenerating normal liver cells, causing toxicity to normal tissues.

DISCLOSURE

Technical Problem

Under these circumstances, the inventors of the present invention have made extensive efforts to develop a cancer gene therapy approach with improved tissue specificity and therapeutic efficacy and, as a result, have found that it is possible to maintain high tissue specificity, provide excellent cancer tissue-specific therapeutic effects, and significantly reduce side effects caused by gene therapy by additionally linking a nucleic acid sequence recognizing a micro RNA-122a (microRNA-122a, miR-122a) to a cancer tissue-specific trans-splicing ribozyme, to which a splicing donor/splicing acceptor sequence (SD/SA sequence) and a woodchuck hepatitis virus posttranscriptional regulatory element (WPRE) are further linked, thereby completing the present invention.

Technical Solution

An object of the present invention is to provide a recombinant vector comprising: (i) a tissue-specific promoter; and (ii) a ribozyme-target gene expression cassette comprising a trans-splicing ribozyme targeting a cancer-specific gene and a target gene linked to the 3' exon of the ribozyme, wherein a splicing donor/splicing acceptor sequence (SD/SA sequence) is linked to the 5' end of the ribozyme-target gene expression cassette and a woodchuck hepatitis virus post-transcriptional regulatory element (WPRE) is linked to the 3' end of the ribozyme-target gene expression cassette, and wherein (iii) a nucleic acid sequence recognizing a micro RNA-122a (microRNA-122a, miR-122a) is further linked to the 3' end of the WPRE.

Another object of the present invention is to provide a transformed cell into which the recombinant vector is introduced.

Still another object of the present invention is to provide a ribozyme expressed from the recombinant vector.

Yet another object of the present invention is to provide a pharmaceutical composition for preventing or treating hepatocellular carcinoma, comprising the recombinant vector or the ribozyme as an active ingredient.

Still yet another object of the present invention is to provide a method for treating hepatocellular carcinoma, comprising administering to a subject in need thereof a pharmaceutically effective amount of the recombinant vector or the ribozyme.

Advantageous Effects

The recombinant vector of the present invention and the ribozyme expressed therefrom, which comprise a tissue-specific promoter, SD/SA and WPRE for improving the expression level of the ribozyme, and a tissue-specific microRNA target site, can increase the expression efficiency and reduce the toxicity to normal tissues, which in turn increase both the therapeutic effect and safety, and thus can be widely used in the field of gene therapy in the future.

DESCRIPTION OF DRAWINGS

FIGS. 9A and 9B show the results of treatment of orthotopic multiple hepatocellular carcinoma mouse models, in which tumor was implanted in the spleen, with PBS as a negative control, Ad-PRT-122aT ($10 \times 10^{10}$) as a positive control, and adenovirus Ad-EPRT-122aT of the present invention at various concentrations ($10 \times 10^{10}$, $2 \times 10^{10}$, $1 \times 10^{10}$ and $0.5 \times 10^{10}$), in which FIG. 9A shows the tumor tissue weight, and FIG. 9B shows the AST and ALT levels measured simultaneously.

MODE FOR INVENTION

Figure 1:
FIG. 1 is a schematic diagram showing the structure of a trans-splicing ribozyme derivative of the present invention.

To achieve the above objects, an embodiment of the present invention provides a recombinant vector comprising: (i) a tissue-specific promoter; and (ii) a ribozyme-target gene expression cassette comprising a trans-splicing ribozyme targeting a cancer-specific gene and a target gene linked to the 3' exon of the ribozyme, wherein a splicing donor/splicing acceptor sequence (SD/SA sequence) is linked to the 5' end of the ribozyme-target gene expression cassette and a woodchuck hepatitis virus posttranscriptional regulatory element (WPRE) is linked to the 3' end of the ribozyme-target gene expression cassette, and wherein (iii) a nucleic acid sequence recognizing a micro RNA-122a (microRNA-122a, miR-122a) is further linked to the 3' end of the WPRE. Specifically, the recombinant vector may comprise a nucleic acid sequence represented by SEQ ID NO: 18.

Based on the fact that the recombinant vector comprising a ribozyme and an SD/SA sequence and WPRE at both ends of a target gene is effective in cancer treatment in vivo, the recombinant vector uses the SD/SA sequence and the WPRE at the same time and further comprises a nucleic acid sequence recognizing a micro RNA-122a (microRNA-122a, miR-122a), enabling treatment specific to cancer cells, particularly hepatocellular carcinoma cells.

As used herein, the term "vector" refers to an expression vector capable of expressing a target gene in appropriate host cells and to a gene construct that includes essential regulatory elements to which a gene insert is operably linked so as to be expressed.

As used herein, the term "operably linked" refers to a functional linkage between a nucleic acid sequence coding for a target protein and a nucleic acid expression regulatory sequence so as to perform general functions. For example, when a ribozyme-coding sequence is operably linked to a promoter, the expression of the ribozyme-coding sequence is placed under the influence or control of the promoter. Two nucleic acid sequences (a ribozyme-coding sequence and a promoter region sequence linked to the 5' end of the coding sequence) are said to be operably linked if the induction of promoter function results in the transcription of the ribozyme-coding sequence, and if the nature of the linkage between the two DNA sequences does not result in the introduction of a frame-shift mutation nor interfere with the ability of the expression regulatory sequences to direct the expression of the ribozyme. The operable linkage to a recombinant vector may be prepared using a genetic recombinant technique well known in the art, and site-specific DNA cleavage and ligation may be easily achieved using enzymes generally known in the art.

The vector of the present invention may include a signal sequence or leader sequence for membrane targeting or secretion as well as expression regulatory elements, such as a promoter, an operator, an initiation codon, a stop codon, a polyadenylation signal and an enhancer, and can be constructed in various forms depending on the purpose thereof. The promoter of the vector may be constitutive or inducible. In addition, expression vectors include a selectable marker that allows the selection of host cells containing the vector, and replicable expression vectors include a replication origin. The vector may be self-replicable, or may be incorporated into the host DNA. The vector includes a plasmid vector, a cosmid vector, a viral vector, etc., and specifically, the vector may be a viral vector. Viral vectors include, but not limited to, vectors derived from retroviruses such as human immunodeficiency virus (HIV), murine leukemia virus (MLV) avian sarcoma/leukosis (ASLV), spleen necrosis virus (SNV), Rous sarcoma virus (RSV), mouse mammary tumor virus (MMTV), etc., adenoviruses, adeno-associated viruses, herpes simplex viruses, etc. More specifically, the recombinant vector of the present invention may be a recombinant adenoviral vector.

As used herein, the term "expression cassette" refers to a unit cassette which includes a promoter and a trans-splicing ribozyme-target gene, in which an SD/SA sequence and a WPRE sequence are present at the 5' and 3' ends of the trans-splicing ribozyme-target gene, and to which a nucleic acid sequence recognizing a micro RNA-122a (microRNA-122a, miR-122a) is further linked, thereby expressing the trans-splicing ribozyme-target gene.

The ribozyme-target gene expression cassette of the present invention may further comprise a sequence capable of controlling the level of transcripts, i.e., a control derivative, at a sequence to which the ribozyme and the target gene are linked, but not limited thereto. Particularly, a splicing donor/splicing acceptor sequence (SD/SA sequence) and a woodchuck hepatitis virus posttranscriptional regulatory element (WPRE) are linked to the ribozyme-target gene expression cassette of the present invention, in which a nucleic acid sequence recognizing a micro RNA-122a is further linked to the 3' end of the WPRE, thereby controlling the expression level of the ribozyme-target gene and the tissue-specific expression.

Specifically, the ribozyme-target gene expression cassette of the present invention may be a ribozyme-target gene expression cassette in which a splicing donor/splicing acceptor sequence (SD/SA sequence) is linked to the 5' end of the ribozyme, a WPRE sequence is linked to the 3' end of the target gene, and a sequence recognizing a micro RNA-122a is linked to the 3' end of the WPRE.

In the present invention, the SD/SA can promote transcription initiation, processing of RNA polymerase II, and nucleocytoplasmic export of mRNA, and the WPRE can promote processing of mRNA and nucleocytoplasmic export of mRNA, thereby increasing the level of pre-mRNA, respectively.

With the above-described structure, the RNA level of ribozyme in cells is significantly increased and the amount of transcripts is increased to thereby increase cell death of cancer cells in cells and in vivo and induce cancer cell-specific expression, thus reducing the toxicity to normal cells.

In an embodiment of the present invention, when SD/SA and WPRE are further linked to a trans-splicing ribozyme to which a cancer gene therapeutic agent is linked, the expression of the ribozyme increases, which in turn increases the effect of inducing cell death, and when miR-122aT targeting miR-122a is further linked thereto, it does not induce cell death in normal liver cells where the expression of miR-122a normally occurs and induces cell death in hepatocellular carcinoma cells where the expression of miR-122a is reduced, confirming the potential for hepatocellular carcinoma cell-specific treatment.

The SD/SA sequence is a sequence corresponding to the start and end of an intron cleaved in a splicing reaction to remove the intron of an RNA transcript. Generally, the SD sequence may be a GU sequence at the 5' end of the intron, and the SA sequence may be an AG sequence at the 3' end of the intron. In the present invention, the SD/SA sequence may include a nucleic acid sequence of SEQ ID NO: 3, but is not limited thereto as long as it is present in a target gene expression cassette and can promote the expression of a target gene.

The WPRE refers to a sequence that induces a tertiary structure that promotes expression on DNA to thereby increase expression of a gene. In the present invention, the WPRE may have a nucleic acid sequence of SEQ ID NO: 7, but is not limited thereto as long as it is present in a target gene expression cassette and can promote the expression of a target gene.

The nucleic acid sequence recognizing the micro RNA-122a (microRNA-122a, miR-122a) is called miR-122aT (microRNA-122a target site). Micro RNA-122a is normally expressed in normal cells, but the expression level thereof is reduced in hepatocellular carcinoma cells. Thus, it is possible to develop a therapeutic agent having increased sensitivity and specificity to hepatocellular carcinoma cells using the same, and particularly in the present invention, a nucleic acid sequence recognizing microRNA-122a (microRNA-122a, miR-122a) is linked to a ribozyme to which a target gene is linked, thereby inducing causing the expression of hepatocellular carcinoma cell-specific ribozyme.

As used herein, the term "cancer-specific gene" refers to a gene that is expressed specifically in cancer cells or significantly overexpressed in cancer cells. The cancer-specific gene may have a feature that allows the ribozyme according to the present invention to act specifically in cancer cells. Typical examples of this cancer-specific gene may include telomerase reverse transcriptase (TERT) mRNA, alpha-fetoprotein (AFP) mRNA, carcinoembryonic antigen (CEA) mRNA, prostate-specific antigen (PSA) mRNA, and cytoskeleton-associated protein 2 (CKAP2) mRNA, and specifically telomerase reverse transcriptase (TERT) mRNA, more specifically, human telomerase reverse transcriptase (hTERT) mRNA can be used.

As used herein, the term "telomerase reverse transcriptase (TERT)" refers to one of the most important enzymes that regulate the immortality and proliferation ability of cancer cells and refers to an enzyme that forms telomeres that function to protect the chromosomal ends, thereby inhibiting cellular aging. In normal cells, each time the cell divides, the length of telomeres decreases little by little, and as a result, genetic material is lost, and the cell dies. However, in cancer cells, this enzyme continuously extends telomeres, and thus the cells do not die. Moreover, this enzyme is known as an important obstacle in cancer treatment, which contributes directly to the immortality of cancer cells. Germ cells, hematopoietic cells and cancer cells that are infinitely replicated have a telomerase activity of 80 to 90%, but normal cells surrounding cancer cells have no telomerase activity. In the present invention, hTERT mRNA can be uses as a cancer-specific gene, but not limited thereto.

As used herein, the term "promoter" refers to a region of DNA involved in binding of RNA polymerase to initiate transcription. Generally, the promoter is adjacent to a target gene on the same strand as the target gene and located upstream thereof, where an RNA polymerase or a protein associated with the RNA polymerase, i.e., a transcription factor is bound, thereby inducing the enzyme or protein to be located at the correct transcription initiation site. That is, the promoter is located at the 5' site of a gene to be transcribed on the sense strand such that the RNA polymerase is bound to the corresponding location directly or via a transcript to induce the initiation of mRNA synthesis and has a specific gene sequence. To increase gene expression, universal promoters such as LTR of retrovirus, Rous sarcoma Virus (RSV) or cytomegalovirus (CMV) promoters can be used; however, a tissue-specific promoter can be used in the present invention.

As used herein, the term "tissue-specific promoter" refers to a nucleic acid sequence that activates the transcription of promoter downstream gene to mRNA specifically to tissues, in which the upstream of coding region is not decoded. Examples thereof include a phosphoenolpyruvate carboxykinase (PEPCK) promoter as a liver cell-specific promoter, an apolipoprotein E promoter, a serum albumin promoter, a hepatocellular carcinoma-specific alpha-fetoprotein (AFP) promoter, a colon cancer-specific carcinoembryonic antigen (CEA) promoter, and a prostate-specific antigen (PSA) promoter. In the present invention, the promoter may be a liver tissue-specific PEPCK promoter, but not limited thereto. In the present invention the PEPCK promoter may be a promoter comprising a nucleic acid sequence of SEQ ID NO: 2 and may be a promoter further comprising an enhancer that acts on a PEPCK promoter comprising a nucleic acid sequence of SEQ ID NO: 1.

As used herein the term "ribozyme" refers to an RNA molecule that acts like an enzyme or a molecule composed of a protein comprising the RNA molecule and is also called an RNA enzyme or catalytic RNA. It has been found that ribozymes catalyze chemical reactions with RNA molecules with a definite tertiary structure and have catalytic or auto-catalytic properties, some ribozymes cleave themselves or other RNA molecules to inhibit activity, and other ribozymes catalyze the aminotransferase activity of ribosomes. Such ribozymes may include hammerhead ribozymes, VS ribozymes, hairpin ribozymes, etc. In the present invention, the ribozyme inhibits the activity of a cancer-specific gene through a trans-splicing reaction, resulting in selective anti-cancer effect, and is expressed in a form conjugated with an anti-cancer therapeutic gene to active the anti-cancer therapeutic gene. Therefore, any form can be used as long as it is capable of inactivating the cancer-specific gene and activating the anti-cancer therapeutic gene. Specifically, the ribozyme may comprise a nucleic acid sequence of SEQ ID NO: 5.

For the purpose of the present invention, the ribozyme of the present invention is a ribozyme targeting the above-described hTERT mRNA and serves to specifically cleave and inhibit hTERT mRNA by targeting cancer cells overexpressing hTERT, particularly hepatocellular carcinoma cells, and specifically express herpes simplex virus-thymidine kinase (HSVtk) gene, which is a therapeutic gene. Moreover, the ribozyme of the present invention plays an important role in targeting and treating cancer cells without toxicity to normal cells by allowing the recombinant vector capable of expressing the ribozyme to reach the liver by a carrier such as adenovirus, etc.

As used herein, the term "trans-splicing" refers to the linkage of RNAs from different genes. Specifically, an hTERT-targeting tans-splicing group I ribozyme, which has been proven to have the ability of trans-splicing by recognizing mRNA of cancer-specific human Telomerase reverse transcriptase (hTERT) may be used.

Meanwhile, the inventors of the present invention have devised a recombinant adenovirus capable of expressing a target gene in addition to the ribozyme. That is, the recombinant adenovirus may function to insert a target gene, which is contained in a target gene expression cassette linked to a ribozyme through a trans-splicing ribozyme specific to a cancer-specific gene, into a cancer-specific gene transcript.

As used herein, the term "target gene" refers to a gene that is linked to mRNA of a cancer-specific gene by the ribozyme and is expressed, and in the present invention, it may be a therapeutic gene or a reporter gene, but not limited thereto.

As used herein, the term "anti-cancer therapeutic gene" refers to a polynucleotide sequence encoding a polypeptide that exhibits a therapeutic effect upon expression in cancer cells. In the present invention, the anti-cancer therapeutic gene can be expressed in a form conjugated with the ribozyme or expressed independently to exhibit anti-cancer activity. Examples of this anti-cancer therapeutic gene may include, but not limited to, drug-sensitizing genes, proapoptotic genes, cytostatic genes, cytotoxic genes, tumor suppressor genes, antigenic genes, cytokine genes, anti-angiogenic genes, etc., and in the present invention, the anti-cancer therapeutic gene may be used alone or in combination of two or more.

As used herein, the term "drug-sensitizing gene" refers to a gene for an enzyme that converts a nontoxic prodrug into a toxic form and is also called a suicide gene, as cells transfected with the gene die. That is, when a prodrug that is non-toxic to normal cells is systemically administered, the prodrug is converted into toxic metabolites only in cancer cells by the drug-sensitizing gene to change drug sensitivity to thereby kill cancer cells. Typical examples of the drug-sensitizing gene may include, but are not limited to, herpes simplex virus-thymidine kinase (HSV-tk) gene, ganciclovir, an *E. coli* cytosine deaminase (CD) gene, 5-fluorocytosine (5-FC), etc.

As used herein, the term "proapoptotic gene" refers to a nucleotide sequence that is expressed to induce programmed cell death. Examples of the proapoptotic gene may include those known in the art such as p53, adenovirus E3-11.6K (derived from Ad2 and Ad5) or adenovirus E3-10.5K (derived from Ad), adenovirus E4 gene, p53 pathway gene, and caspase-coding gene.

As used herein, the term "cytostatic gene" refers to a nucleotide sequence that is expressed in cells to stop the cell cycle. Examples thereof may include, but not limited to, p21, retinoblastoma gene, E2F-Rb fusion protein gene, cyclin-dependent kinase inhibitor-encoding genes (e.g., p16, p15, p18, and p19), growth arrest specific homeobox (GAX) genes, etc.

As used herein, the term "cytotoxic gene" refers to a nucleotide sequence that is expressed in cells to exhibit a toxic effect. Examples of thereof may include, but not limited to, nucleotide sequences that encode *Pseudomonas* exotoxin, lysine toxin, *diphtheriae* toxin, etc.

As used herein, the term "tumor suppressor gene" refers to a nucleotide sequence that is expressed in target cells to inhibit tumor phenotypes or induce apoptosis. Examples thereof may include tumor necrosis factor-α (TNF-α), p53 gene, APC gene, DPC-4/Smad4 gene, BRCA-1 gene, BRCA-2 gene, WT-1 gene, retinoblastoma gene, MMAC-1 gene, adenomatous polyposis coil protein, deleted colorectal carcinoma (DCC) gene, MMSC-2 gene, NF-1 gene, ENT tumor suppressor gene located in chromosome 3p21.3, MTS1 gene, CDK4 gene, NF-1 gene, NF-2 gene, VHL gene, and sPD-1 (programmed death-1).

As used herein, the term "antigenic gene" refers to a nucleotide sequence which is expressed in target cells to produce a cell surface antigenic protein that can be recognized in the immune system. Examples of the antigenic gene known to those skilled in the art may include carcinoembryonic antigen (CEA) and p53.

As used herein, the term "cytokine gene" refers to a nucleotide sequence which is expressed in cells to produce cytokine. Examples thereof may include GM-CSF, interleukins (IL-1, IL-2, IL-4, IL-12, IL-10, IL-19 and IL-20), interferon α, β and γ (interferon α-2b), and fusions such as interferon α-2α-1.

As used herein, the term "anti-angiogenic gene" refers to a nucleotide sequence which is expressed in cells to release anti-angiogenic factors out of the cells. Examples thereof may include angiostatin, inhibitors of vascular endothelial growth factor (VEGF), endostatin, etc.

Figure 4:
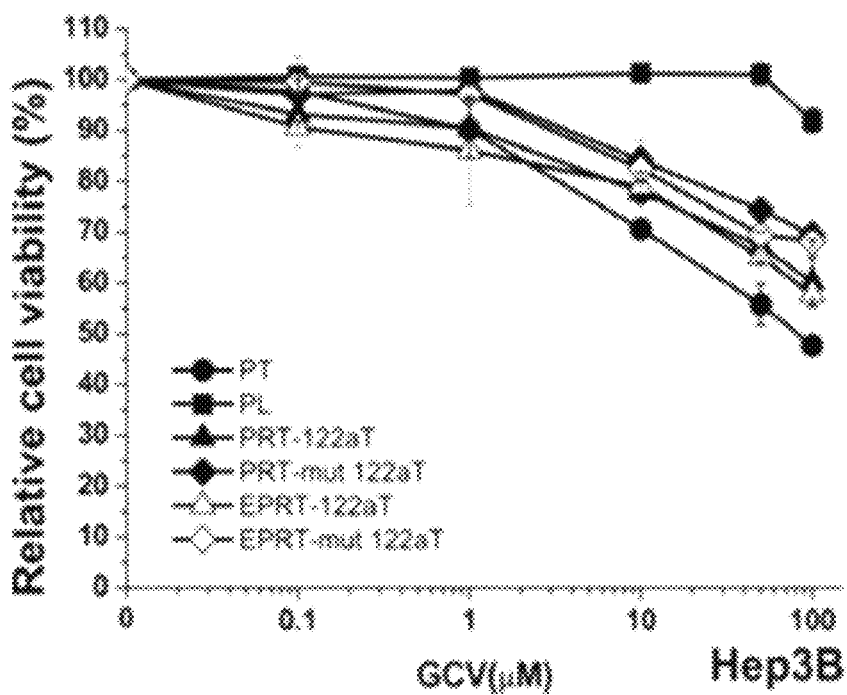
FIG. 4 is a graph showing the increased induction of cell death by transduction of ribozymes (EPRT-122aT, EPRT-mut 122aT), to which SD/SA and WPRE are linked, into Hep3B (miR-122a−) cells.

In an embodiment of the present invention, a recombinant vector is constructed, which can express HSVtk, a kind of anti-cancer therapeutic genes, in a form conjugated to a ribozyme that targets hTERT, can exhibit high expression efficiency by containing an SD/SA sequence and/or a WPRE sequence, and can be expressed specifically in hepatocellular carcinoma cells by further containing a miR-122aT sequence, and it was found that the introduction of a recombinant vector containing both SD/SA and WPRE increased the expression level (FIG. 4). Moreover, it was observed that the treatment of cells, in which the level of miR-122a was reduced, with the recombinant vector increased the induction of cell death, compared to cells in which miR-122a expressed normally (FIGS. 5 to 7), and thus it was found that it is possible to selectively treat hepatocellular carcinoma cells by distinguishing normal cells in which miR-122a expressed normally and hepatocellular carcinoma cells in which the expression of miR-122a was reduced.

Figure 11:
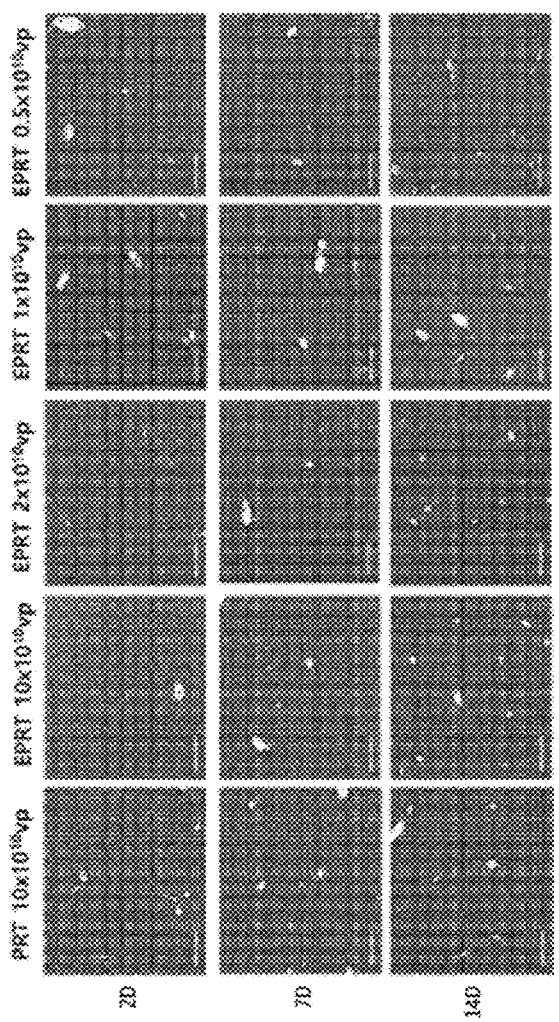
FIG. 11 shows images of mouse livers with H&E staining after treatment of orthotopic multiple hepatocellular carcinoma mouse models, in which tumor was implanted in the spleen, with PBS as a negative control, Ad-PRT-122aT ($10 \times 10^{10}$) as a positive control, and adenovirus Ad-EPRT-122aT of the present invention at various concentrations ($10 \times 10^{10}$, $2 \times 10^{10}$, $1 \times 10^{10}$ and $0.5 \times 10^{10}$).
Figure 12:
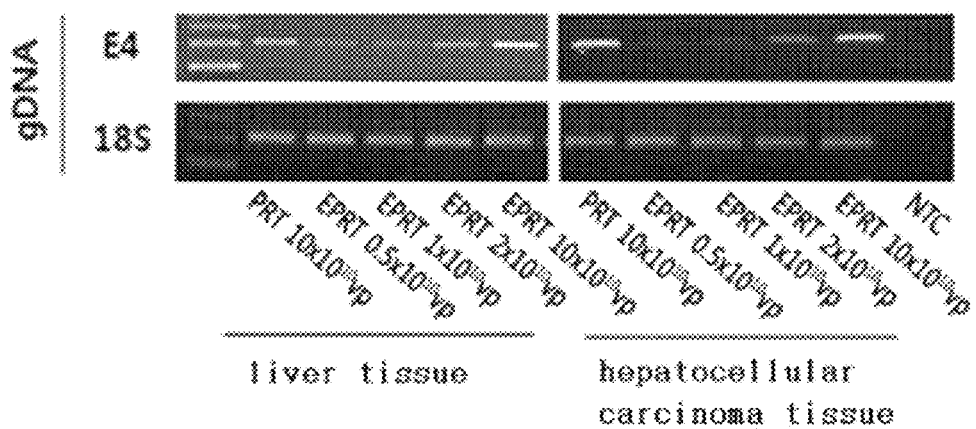
FIG. 12 shows the degree of introduction of adenoviral vectors from the amount of gDNA extracted from normal tissues and hepatocellular carcinoma tissues, determined at the molecular level, after systemic treatment of xenograft models (orthotopic multiple hepatocellular carcinoma models), in which tumor was implanted in the spleen, with Ad-PRT-122aT ($10 \times 10^{10}$), Ad-EPRT-122aT ($10 \times 10^{10}$), Ad-EPRT-122aT ($2 \times 10^{10}$), Ad-EPRT-122aT ($1 \times 10^{10}$), and Ad-EPRT-122aT ($0.5 \times 10^{10}$), respectively.

Furthermore, in an embodiment of the present invention, it was found that as a result of treating orthotopic multiple hepatocellular carcinoma mouse models with the adenovirus (Ad-EPRT-122aT) of the present invention, the adenovirus was not cytotoxic to normal cells (FIG. 8), and that even with a dose of ¹/₁₀ of that of the existing adenovirus (Ad-PRT-122aT), it exhibited a higher anticancer effect than the existing adenovirus (FIGS. 9A, 9B, 10 and 11), and that even with a dose of ¹/₁₀ of that of Ad-PRT-122aT, and the introduction of adenovirus into normal liver tissues and implanted hepatocellular carcinoma tissues of animal models was confirmed at the molecular level (FIG. 12).

Therefore, it is possible to further increase the cancer-specific therapeutic effect by increasing the induction of cell death of hepatocellular carcinoma cells and inhibiting the cell death of normal cells to minimize side effects using the trans-splicing ribozyme of the present invention to which SD/SA, WPRE, and miR-122aT are further linked, and to which a cancer gene therapeutic agent is linked.

As used herein, the term "herpes simplex virus-thymidine kinase (HSV-tk)" refers to a thymidine phosphorylase derived from herpes simplex virus. This enzyme is a representative example of the drug-sensitizing genes that convert a nontoxic prodrug into a toxic substance to causes the cells transfected with the gene to die. In the present invention, the HSVtk gene is expressed in a form conjugated with the ribozyme according to the present invention and can be used as an anti-cancer therapeutic gene that exhibits anti-cancer activity. Specifically, this HSVtk gene may include a nucleic acid sequence represented by SEQ ID NO: 6, and may include those with accession numbers AAP13943, P03176, AAA45811, P04407, Q9QNF7, KIBET3, P17402, P06478, P06479, AAB30917, P08333, BAB84107, AAP13885, AAL73990, AAG40842, BAB11942, NP_044624, NP_044492, CAB06747, etc. assigned by GenBank.

As used herein, the term "reporter gene" refers to a gene used for monitoring the introduction of the recombinant vector of the present invention or the expression efficiency of ribozymes, and any gene that can be monitored without damage to infected cells or tissues can be used without limitation. Examples thereof may include luciferase, green fluorescent protein (GFP), modified green fluorescent protein (mGFP), enhanced green fluorescent protein (EGFP), red fluorescent protein (RFP), modified red fluorescent protein (mRFP), enhanced red fluorescent protein (ERFP), blue fluorescent protein (BFP), modified blue fluorescent protein (EBFP), yellow fluorescent protein (YFP), modified yellow fluorescent protein (EYFP), cyan fluorescent protein (CFP), and modified cyan fluorescent protein (ECFP).

The expression level of cancer cell-specific ribozyme can be observed by inserting a reporter gene as a target gene. In particular, the ribozyme of the present invention comprising a tissue-specific promoter and a microRNA target site is not expressed in normal cells, but expressed specifically in cancer cells, and thus it is obvious to those skilled in the art that it can be applied to diagnose the occurrence of cancer in a specific tissue.

Another embodiment of the present invention provides a transformed cell into which the recombinant vector is introduced.

As used herein, the term "introduction" refers to the insertion of foreign DNA into a cell by transformation or transduction. The transfection may be carried out by various methods known in the art, such as calcium phosphate-DNA coprecipitation, DEAE-dextran-mediated transfection, polybrene-mediated transfection, electroporation, microinjection, liposome fusion, lipofectamine and protoplast fusion, etc. Moreover, the transfection can deliver a gene into a cell using a virus or viral vector particle by means of infection.

As used herein, the term "transformed cell" refers to a cell in which a target polynucleotide is introduced into a host cell. The transformation may be made by the "introduction" and may be carried out by selecting an appropriate standard technique depending on the host cell as is known in the art. In an embodiment of the present invention, a transformed cell, into which a recombinant vector is introduced, is prepared by injecting the recombinant vector into the cell using PEI or using adenovirus as a carrier, and the transformed cell may be prepared by a method for constructing stable cell lines, instead of transient transfection.

Specifically, the transformed cell of the present invention may be a transformed cell into which a recombinant vector is introduced, the recombinant vector comprising (i) a tissue-specific promoter; and (ii) a ribozyme-target gene expression cassette comprising a trans-splicing ribozyme targeting a cancer-specific gene and a target gene linked to the 3' exon of the ribozyme, wherein a splicing donor/splicing acceptor sequence (SD/SA sequence) is linked to the 5' end of the ribozyme-target gene expression cassette and a woodchuck hepatitis virus posttranscriptional regulatory element (WPRE) is linked to the 3' end of the ribozyme-target gene expression cassette, and wherein (iii) a nucleic acid sequence recognizing a micro RNA-122a (microRNA-122a, miR-122a) is further linked to the 3' end of the WPRE.

Still another embodiment of the present invention provides a ribozyme expressed from the recombinant vector. The recombinant vector and the ribozyme are as described above.

Yet another embodiment of the present invention provides a pharmaceutical composition for preventing or treating hepatocellular carcinoma, comprising the recombinant vector or the ribozyme as an active ingredient.

As used herein, the term "cancer" refers to a condition in which cells have abnormally proliferated due to abnormalities in the function of regulating the division, differentiation and death thereof and invaded the surrounding tissue and organ to form a mass and destroy or modify existing structures, and specifically the cancer may be hepatocellular carcinoma.

As used herein, the term "preventing" refers to all actions that inhibit cancer or delay the development of cancer by administering the recombinant adenovirus or composition of the present invention.

As used herein, the term "treating" refers to all actions that alleviate or beneficially change cancer by administering the recombinant adenovirus or composition of the present invention.

In addition, the pharmaceutical composition for preventing or treating hepatocellular carcinoma of the present invention may further comprise a pharmaceutically acceptable carrier, excipient or diluent.

Examples of the pharmaceutically acceptable carrier, excipient or diluent that can be used in the pharmaceutical composition of the present invention may include lactose, dextrose, sucrose, sorbitol, mannitol, xylitol, erythritol, maltitol, starch, acacia gum, alginate, gelatin, calcium phosphate, calcium silicate, calcium carbonate, cellulose, methyl cellulose, polyvinyl pyrrolidone, water, methyl hydroxybenzoate, propyl hydroxybenzoate, talc, magnesium stearate, mineral oil, etc.

The pharmaceutical composition of the present invention may be formulated according to conventional methods in oral dosage forms such as powders, granules, tablets, capsules, suspensions, emulsions, syrup and aerosol, preparations for external application, suppositories, and sterile injectable solutions. The composition of the present invention may be formulated with commonly used diluents or excipients, such as fillers, extenders, binders, wetting agents, disintegrants, surfactants, etc. Examples of solid formulations for oral administration may include tablets, pills, powders, granules, capsules, etc., and such solid formulations comprise at least one excipient, for example, starch, calcium carbonate, sucrose, lactose or gelatin. In addition to simple excipients, lubricants such as magnesium stearate or talc may also be used.

Liquid formulations for oral administration may include suspensions, solutions, emulsions, and syrup, and may contain various excipients, for example, wetting agents, flavoring agents, aromatics and preservatives, in addition to water and liquid paraffin, which are frequently used simple diluents.

Formulations for parenteral administration may include sterilized aqueous solutions, non-aqueous solutions, suspensions, emulsions, freeze-dried preparations, and suppositories. As non-aqueous solvents or suspending agents, propylene glycol, polyethylene glycol, plant oils such as olive oil, injectable esters such as ethyl oleate, etc. can be used. As the base of the suppositories, Witepsol, Macrogol, Tween 61, cacao butter, laurin fat, glycerogelatin, etc. can be used.

Still yet another embodiment of the present invention provides a method for treating hepatocellular carcinoma, comprising administering to a subject in need thereof a pharmaceutically effective amount of the recombinant vector or the ribozyme.

As used herein, the term "pharmaceutically effective amount" refers to an amount sufficient to treat disease at a reasonable benefit/risk ratio applicable to any medical treatment. The effective dosage level of the composition may be determined depending on the patient' sex and age, the type and severity of disease, the activity of a drug, the sensitivity to the drug, the time of administration, the route of administration, the excretion rate, the duration of treatment, factors including co-used drugs, and other factors known in the medical field. The pharmaceutical composition of the present invention may be administered individually or in combination with other therapeutic agents, and may be administered sequentially or simultaneously with conventional therapeutic agents. The composition of the present invention also can be administered in a single or multiple dosage form. It is important to administer the composition in the minimum amount that can exhibit the maximum effect without causing side effects in view of all the above-described factors, and this amount can be easily determined by a person skilled in the art.

As used herein, the term "subject" refers to all the animals including humans such as horses, sheep, pigs, goats, camels, antelopes, dogs, etc. with cancers that can be improved by administering the pharmaceutical composition according to the present invention. It is possible to effectively prevent and treat cancer by administering the pharmaceutical composition according to the present invention to a subject. The method according to the present invention may be a method for treating a non-human subject, but not limited thereto. That is, given that humans have cancers that can be improved by administering the pharmaceutical composition according to the present invention, it can be sufficiently used in the treatment of humans.

As used herein, the term "administering" refers to introducing a predetermined substance into an animal by any suitable method. The pharmaceutical composition of the present invention may be administered by any general route, as long as it can reach a target tissue. In addition, the pharmaceutical composition of the present invention may be administered using any device capable of delivering the active ingredient to target cells.

The preferred dosage of the pharmaceutical composition according to the present invention may vary depending on the patient's conditions and weight, the severity of disease, the type of formulation, the route of administration and the duration of treatment, but may be selected appropriately by a person skilled in the art. However, for desired effects, the pharmaceutical composition of the present invention may be administered in a daily dosage of 1 to 10 mg/kg, and preferably 1 to 5 mg/kg. The daily dosage may be taken in a single dose, or may be divided into several doses.

The pharmaceutical composition of the present invention may be administered alone or in combination with other known anticancer drugs or used in combination with auxiliary therapeutic methods such as surgical therapy to increase the anticancer effect. Chemotherapeutic agents that may be used together with the composition of the present invention may include cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin, methotrexate, etc. In addition, radiotherapies that may be used together with the composition of the present invention may include X-ray irradiation and γ-ray irradiation.

BEST MODE FOR CARRYING OUT THE INVENTION

Hereinafter, the present invention will be described in detail with reference to Examples. However, the following Examples are only illustrative of the present invention, and the present invention is not limited by the following Examples.

Example 1: Construction of Recombinant Vectors 1-1. Construction of pAVQ PEPCK-SD/SA-Ribozyme-TK-WPRE-122aT(3×) Plasmids In the present invention, in order to induce the expression of a trans-splicing ribozyme to which a tissue-specific cancer gene therapeutic agent is linked, an optimal configuration has been prepared using a PEPCK promoter (SEQ ID NO: 2) as a liver cell-specific promoter, a splicing donor/splicing acceptor (SD/SA) sequence (SEQ ID NO: 3) as a control derivative, a woodchuck hepatitis virus posttranscriptional regulatory element (WPRE) (SEQ ID NO: 7), and miR-122aT. The term "miR-122aT" refers to a nucleic acid sequence (miR-122a target site (miR-122aT) recognizing a micro RNA-122a (microRNA-122a, miR-122a) expressed specifically in liver cells. Moreover, the term "TK" refers to herpes simplex virus thymidine kinase (HS-Vtk) (SEQ ID NO: 6) as an anti-HSV gene therapeutic agent, which was used as one of the gene therapeutic agents.

Cloning was carried out to insert SD/SA into the 5' upstream of a T/S ribozyme (hTERT targeting T/S ribozyme; targeting +21 region of hTERT and containing an antisense sequence for +30 to +324 regions, extended P1 helix, and P10 region of 6 nucleotide) and insert WPRE behind TK linked to the ribozyme as follows.

Specifically, based on a pAVQ PEPCK Ribozyme TK vector, a vector was prepared, which comprises a splicing donor/splicing acceptor (SD/SA) at the 5' end of a ribozyme-target gene, a woodchuck hepatitis virus posttranscriptional regulatory element (WPRE) at the 3' end of the ribozyme-target gene, and miR-122aT.

First, in order to insert the SD/SA into the pAVQ PEPCK Ribozyme TK vector, the vector was cleaved with restriction enzyme BglII (Fermentas) to remove from the antisense region of ribozyme to the intermediate region of the ribozyme. Moreover, for an insert to be inserted, a pAVQ SD/SA CRT (see Korean Patent Application No. 10-2013-0099276) into which the SD/SA was inserted was cleaved with restriction enzyme BglII (Fermentas) to obtain from the SD/SA to the intermediate region of the ribozyme.

The resulting vector and insert were mixed at a ratio of 1:10 and then ligated using T4 DNA ligase (Roche) at 4° C. overnight.

The ligated vector was transformed into DH5α *E. coli* competent cells by heat shock transformation, spread uniformly on an agar plate containing kanamycin, and cultured in an incubator at 37° C. for 16 hours. Colonies grown on the agar plate were inoculated into LB medium supplemented with kanamycin, and DNA was extracted with mini-prep to identify clones containing the vector with the insert.

In order to insert the WPRE into the pAVQ PEPCK SD/SA Ribozyme TK into which the SD/SA was inserted by the cloning, the vector was cleaved with restriction enzyme FseI (Fermentas). Moreover, a pAVQ CRT WPRE (see Korean Patent Application No. 10-2013-0099276) into which the WPRE was inserted was amplified with primers (SEQ IS NO: 10; forward primer—5'-GCGGCCGGC-CAATCAACCTCTGGATTACAAA-3', SEQ IS NO: 11; reverse primer—5'-GCGGCCGGCCGCGGGGAGGCG-GCCCAAA-3') containing an FSEI restriction site as a template and cleaved with restriction enzyme FseI (Fermentas) to prepare inserts.

The resulting vector and insert were mixed at a ratio of 1:10, followed by ligation, and then clones were obtained by transfection.

The resulting pAVQ SD/SA PEPCK Ribozyme TK WPRE vector was cleaved with NotI (Fermentas), and three copies of miR-122aT (TGGAGTGTGACAATGGTGTTTG X3; miR-122a target sequence) were amplified with primers (SEQ ID NO: 12; forward primer—5'-ATAAGAATGCG-GCCGCACAAACACCATTGTCACACT CCACGATA-CAAACACCATTGTCACACTC-3' and SEQ ID NO: 13; reverse primer—5'-ATAAGAATGCGGCCGCTGGAGT-GTGACAATGGTGTTTGTATCGTGGAGTGT-
GACAATGGTG TTTG-3') containing a NotI restriction site to prepare inserts.

The prepared vector and insert were mixed at a ratio of 1:10, followed by ligation, and then clones were obtained by transfection. The obtained clones were named EPRT-122aT.

1-2. Preparation of Control Plasmids Based on pAVQ Vector Containing PEPCK Promoter The inventors of the present invention prepared PRT-mut 122aT (PEPCK-Rib-TK-mut 122aT), one of the control plasmids, based on a pAVQ vector.

Specifically, the pAVQ-rib-TK vector was cleaved with NotI (Fermentas), and three copies of miR-122aT (TG-GAGTGTGACAATGGTGTTTG X3; miR-122a target sequence) were amplified with the forward primer of SEQ ID NO: 12 and the reverse primer of SEQ ID NO: 13 containing a NotI restriction site and cleaved with restriction enzyme NotI (Fermentas) to prepare inserts. Moreover, three copies of mut miR-122aT were amplified with the forward primer (SEQ ID NO: 14; 5'-ATAAGAATGCGGCCGCA-CAAACACCATTCCTCACACTGACGATACAAACAC-CATTCCTCAC ACT-3') and the reverse primer (SEQ ID NO: 15; 5'-ATAAGAATGCGGCCGCTCAGTGTGAG-GAATGGTGTTTGTATCGTCAGTGTGAGGAATGGTG TTTG-3') containing a NotI restriction site and cleaved with restriction enzyme NotI (Fermentas) to prepare inserts.

The prepared vector and insert were mixed at a ratio of 1:10, followed by ligation, and then clones were obtained by transfection. The obtained clones were named PRT-mut 122aT.

Moreover, another control plasmid, EPRT-mut 122aT (PEPCK-SD/SA-Rib-TK-WPRE-mut 122aT), was prepared.

Specifically, the prepared pAVQ SD/SA PEPCK Ribozyme TK WPRE vector was cleaved with NotI (Fermentas), and three copies of mut miR-122aT were amplified with the forward primer of SEQ ID NO: 14 and the reverse primer of SEQ ID NO: 15 containing a NOTI restriction enzyme site and cleaved with restriction enzyme NotI (Fermentas) to prepare inserts.

The prepared vector and insert were mixed at a ratio of 1:10, followed by ligation, and then clones were obtained by transfection. The obtained clones were named EPRT-mut 122aT.

PT (PEPCK-TK) and PL (PEPCK-Lacz) used as control plasmids were prepared according to the contents described in International Journal of Cancer 129: 1018-1029 (2011)

⌈Selective and efficient retardation of cancers expressing cytoskeleton-associated protein 2 by targeted RNA replacement⌋.

Figure 2:
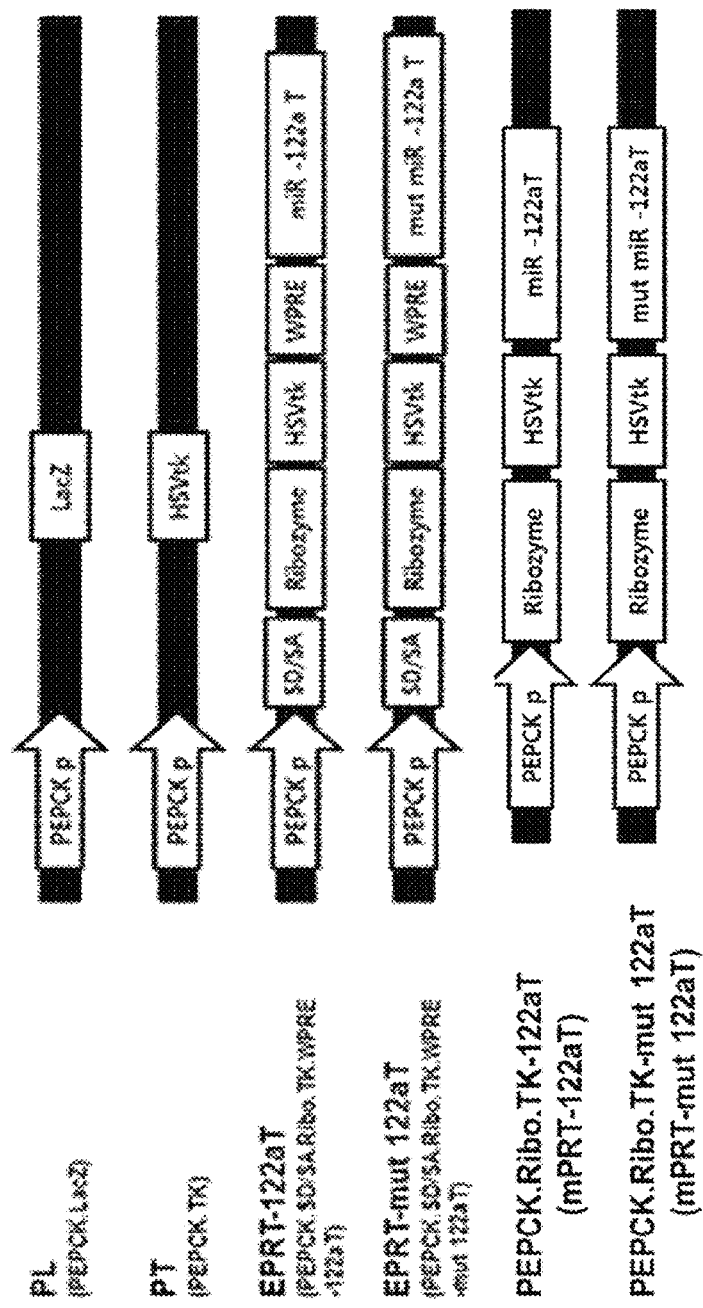
FIG. 2 is a schematic diagram showing PL (PEPCK-Lacz), PT (PEPCK-TK), EPRT-122aT (PEPCK-SD/SA-Rib-TK-WPRE-122aT), EPRT-mut 122aT (PEPCK-SD/SA-Rib-TK-WPRE-mut 122aT), PRT-122aT, and PRT-mut 122aT recombinant vectors constructed by the present invention.

The thus prepared plasmids are shown in a schematic diagram of FIG. 2.

Example 2: Preparation of Recombinant Adenoviruses

In order to prepare adenovirus vectors, constructs cloned into pAdenoVator transfer vectors (Qbiogene) were co-transformed into BJ5183 E. coli strain as competent cells together with pAdenoVator ΔE1/E3 backbone vectors (Qbiogene) for homologous recombination. Transfer vector was linearized with restriction enzyme PmeI (NEB) and purified by phenol extraction and ethanol precipitation, and 1 μg of the obtained DNA and 100 ng of the pAdenoVator ΔE1/E3 backbone vector were co-transformed by electroporation. Recombinant vectors homologously recombined in BJ5183 were linearized with restriction enzyme PacI (NEB) and purified by phenol extraction and ethanol precipitation, followed by transfection into and 293 (Human embryonic kidney) cells using calcium phosphate.

Recombinant vectors amplified in 293 cells were centrifuged at 38,000 rpm in an ultracentrifuge by cesium chloride gradient centrifugation and purified, and the resulting viruses were dialyzed [dH$_2$O 1600 ml, dialysis buffer (100 mM Tris-Cl pH 7.5, 10 mM MgCl$_2$) 200 ml, 100% Glycerol 200 ml] for 2 hours, 2 hours and 16 hours, divided into aliquots and kept at −80° C. The titer of the recombinant virus was determined by TCID50 (tissue culture infectious dose for 50% of the cells) in plaque forming units (pfu).

Example 3: Cell Culture

Human hepatocellular carcinoma cell lines, Hep3B, Huh7, Huh7.5 and HepG2 cells, and human lung adenocarcinoma cell line, SKLU-1, were used.

Cells cultured in an incubator kept at 37° C. and 5% CO$_2$ in minimum essential medium (MEM)/Dulbecco's modified eagle medium (DMEM) supplemented with 10% FBS and 1% penicillin/streptomycin.

Cells were subcultured in new 100 mm culture dishes every 2-3 days. Specifically, the culture dishes to which the cells were attached were washed with 1×PBS (Phosphate buffered saline, 8 g NaCl, 0.2 g KCl, 1.14 g Na$_2$HPO$_4$, 0.2 g KH$_4$PO$_4$/L), treated with 1 ml of 1× Trypsin/EDTA (8.2 g NaCl, 0.2 g KCl, 1.14 g Na$_2$HPO$_4$, 0.2 g KH$_2$PO$_4$, 0.029 g Na$_2$EDTA.dH$_2$O, 1 g trypsin, pH 7.35/L), and then placed in a CO$_2$ incubator for 1 hour. Trypsin was inactivated with 4 mL of medium, and the cells were centrifuged at 1,500 rpm for 2 minutes and 30 seconds to remove the supernatant and resuspended in the medium, followed by subculture.

Example 4: Confirmation of Increased Expression of Ribozyme to which SD/SA and WPRE were Further Linked In order to determine the efficiency of ribozyme to which both SD/SA and WPRE were further linked, the expression level was measured. Specifically, PRT-122aT, PRT-mut 122aT, EPRT-122aT and EPRT-mut 122aT prepared in Example 1-2 were transduced into hepatocellular carcinoma cell lines, Hep3B cells (hTERT+, miR-122a−), respectively, and then the expression level of HSVtk was measured by real-time PCR and compared with the expression level of ribozyme. PT expressing only herpes simplex virus thymidine kinase (HSVtk) as an anti-HSV gene therapeutic agent was used.

The real-time PCR (Corbett-Rotor gene-6000) was carried out by preheating the cells using 5× Phire buffer, 10× SyBr (Invitrogen), 0.14 mM dNTP (NEB), 0.14 uM of 5' and 3' primers, and Phire taq polymerase (0.5 U, Finnzyme), followed by annealing at 60° C. for 30 seconds, 35 cycles of elongation at 72° C. for 30 seconds, and incubation for 8 minutes.

cDNA was amplified with a TK-specific binding primer

```
Forward primer sequence
(SEQ ID NO: 16; 5'-TGACTTACTGGCAGGTGCTG-3')

Reverse primer sequence
(SEQ ID NO: 17; 5'-CCATTGTTATCTGGGCGCTTG-3')
```

Figure 3:
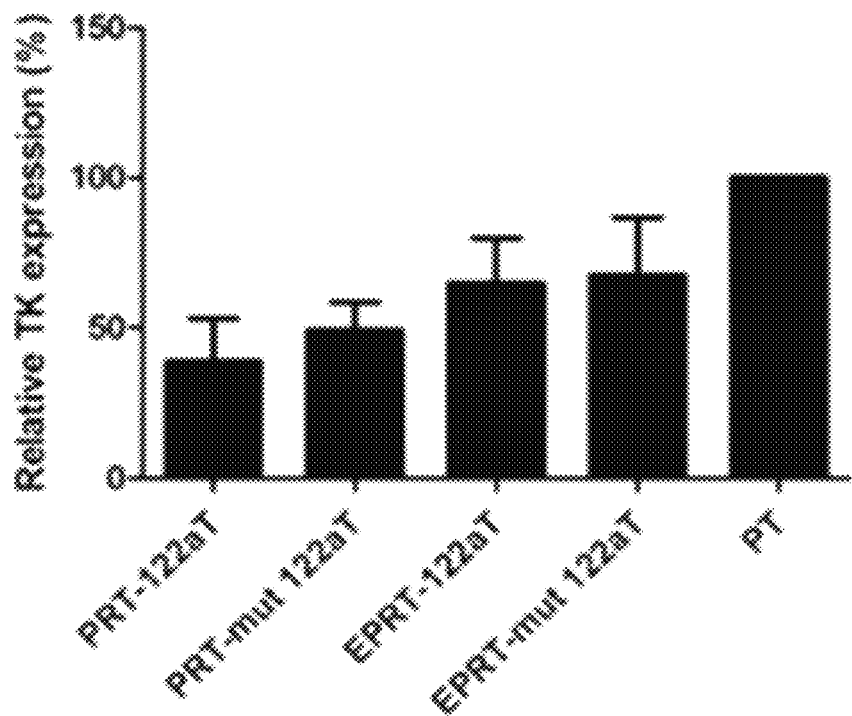
FIG. 3 is a graph showing the increased expression of ribozyme, to which SD/SA and WPRE are further linked, confirmed by real time-PCR.

As shown in FIG. 3, if was found that the expression level was increased when the recombinant vectors, EPRT-122aT and EPRT-mut 122aT, expressing the ribozyme to which SD/SA and WPRE were linked, were introduced, compared to cells into which recombinant vectors, PRT-122a and PRT-mut 122aT, expressing the ribozyme to which SD/SA and WPRE were not linked, were introduced.

As a result, it was found that the expression of the ribozyme to which cancer gene therapeutic agents such as HSVtk, etc. were linked increased when SD/SA and WPRE were further linked to the ribozyme, which can increase the therapeutic effect for hepatocellular carcinoma cells and can increase the efficiency of the cancer gene therapeutic agents based on the trans-splicing ribozyme.

Example 5: Confirmation of Induction of Hepatocellular Carcinoma Cell-Specific Cell Death The plasmid prepared in Example 1, into which SD/SA and WPRE were inserted to increase the efficiency and a nucleic acid sequence (miR-122aT) targeting miR-122a for controlling the liver tissue-specific expression, which is expressed in normal liver tissues but less expressed in hepatocellular carcinoma cells, was inserted three times (3 copies) and the plasmid as a negative control into which mut-122aT was inserted were compared to evaluate the control of miR-122 and the induction of cell death specifically in hepatocellular carcinoma cells for a therapeutic effect.

5-1. Transient MTS Assay

Recombinant vectors prepared in Example 1-2, PT (PEPCK-TK), PRT-122aT (PEPCK-Rib-TK-122aT), EPRT-122aT (PEPCK-SD/SA-Rib-TK-WPRE-122aT), and EPRT-mut 122aT (PEPCK-SD/SA-Rib-TK-WPRE-mut 122aT) were transduced into Hep3B (hTERT+, miR-122a−), Huh7 (hTERT+, miR-122a+), and Huh7.5 (hTERT+, miR-122a+) cells, respectively.

Specifically, $10^6$ cells were seeded in a 35 mm dish, and after 1 week, each 2 μg of cells were transfected with PT (PEPCK-TK), PRT-122aT (PEPCK-Rib-TK-122aT), EPRT-122aT (PEPCK-SD/SA-Rib-TK-WPRE-122aT), EPRT-mut 122aT (PEPCK-SD/SA-Rib-TK-WPRE-mut 122aT), and pAVQ vectors using PEI, and then cultured.

After 1 day, each of the cells was subcultured in a 96 well plate at a density of $10^4$ cells per well. Then, for the next 5 days, the media containing GCV were replaced every 2 days, and after 5 days, each medium was supplemented with 20% CellTiter 96® AQueous ONE Solution Cell Proliferation Assay (Promega) to be 100 μl per well in a 96 well plate. Then, the absorbance at 490 nm was measured by Microplate reader model 550 (BioRad) to observe cell survival.

As shown in FIG. 4, if was found that the induction of cell death was increased in HepG2 (miR-122a−) cells into which ribozymes (EPRT-122aT, EPRT-mut 122aT) to which SD/SA and WPRE were linked were transduced, compared to cells into which ribozymes (PRT-122aT, PRT-mut 122aT) to which SD/SA and WPRE were not linked were transduced. From this, it could also be found that the therapeutic effect of the ribozyme to which SD/SA and WPRE were linked on hepatocellular carcinoma cells was increased.

Furthermore, it could be seen that the induction of cell death of hepatocellular carcinoma cells was increased by transduction of recombinant vectors, PRT-122aT and EPRT-122aT, in which miR-122aT was further linked to a trans-splicing ribozyme to which a cancer gene therapeutic agent was linked, into the cells, compared to cells into which a recombinant vector to which mut-122aT was linked was introduced.

Figure 5A:
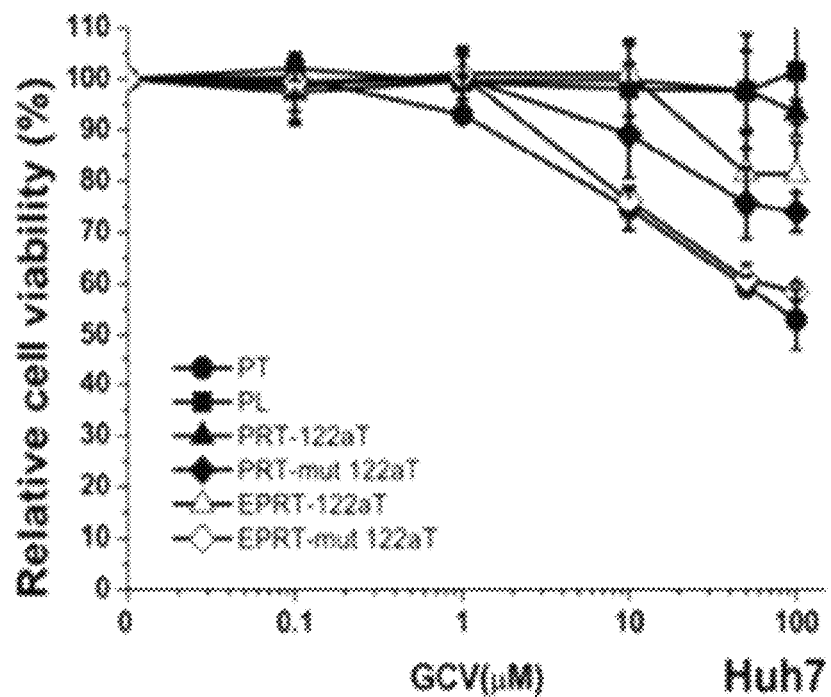
FIG. 5A is a graph showing the reduced cell death, observed by MTS assay, by transduction of recombinant vectors, PRT-122aT and EPRT-122aT, in which miR-122aT is further linked to a trans-splicing ribozyme to which a cancer gene therapeutic agent is linked, into Huh7 (miR-122a+) cells, compared to cells into which a recombinant vector to which mut-122aT is linked is introduced.
Figure 5B:
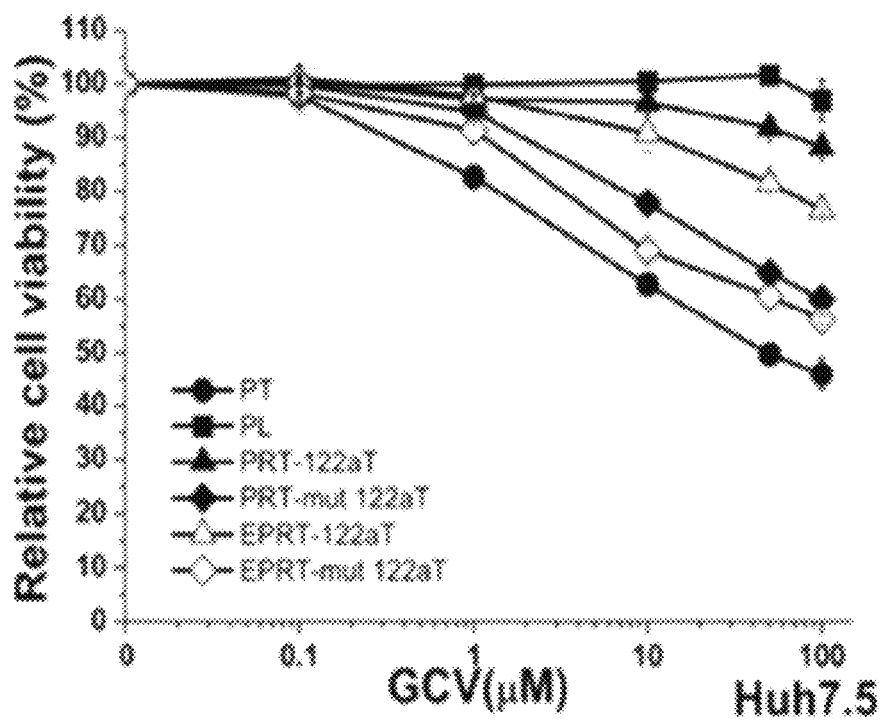
FIG. 5B is a graph showing the reduced cell death, observed by MTS assay, by transduction of recombinant vectors, PRT-122aT and EPRT-122aT, in which miR-122aT is further linked to a trans-splicing ribozyme to which a cancer gene therapeutic agent is linked, into Huh7.5 (miR-122a+) cells, compared to cells into which a recombinant vector to which mut-122aT is linked is introduced.

Moreover, the same recombinant vectors as above were transduced into Huh 7 and Huh7.5 (miR-122a+) cells to obverse cell death. As shown in FIGS. 5A and 5B, it was found that the cell death of cells in which miR-122a was expressed was reduced by transduction of recombinant vectors, PRT-122aT and EPRT-122aT, in which miR-122aT was further linked to a trans-splicing ribozyme to which a cancer gene therapeutic agent was linked, into the cells, compared to cells into which a recombinant vector to which mut-122aT was linked was introduced.

From the above results, it could be seen that the ribozyme into which miR-122aT recognizing miR-122a, which is known to be expressed specifically in normal liver cells, but less expressed in hepatocellular carcinoma cells, is inserted can induce cell death specifically in hepatocellular carcinoma (miR-122a−) cells, which exhibits a therapeutic effect specifically in hepatocellular carcinoma cells.

5-2. Adenoviral Vector MTS Assay

The hepatocellular carcinoma cell-specific effect of the ribozyme, which was expressed by transduction of the recombinant vector in which miR-122aT was further linked to a trans-splicing ribozyme to which a cancer gene therapeutic agent was linked, was determined by an assay using virus infection, in addition to the transient assay of Example 5-1.

Specifically, HepG2 (hTERT+, miR122a−) cells and SKLU-1 (hTERT−, miR122a−) cells were seeded in a 96 well plate at a density of $10^4$ cells per well, and after 1 week, transfected with Ad-PT, Ad-PRT-122aT, Ad-EPRT-122aT, and Ad-EPRT-mut 122aT prepared in Example 2, respectively. PBS was used as a control. Then, for the next 5 days, the media containing GCV were replaced every 2 days. After 5 days, each medium was supplemented with 20% CellTiter 96® AQueous ONE Solution Cell Proliferation Assay (Promega) to be 100 μl per well in a 96 well plate. Then, the absorbance at 490 nm was measured by Microplate reader model 550 (BioRad) to observe cell survival.

Figure 6A:
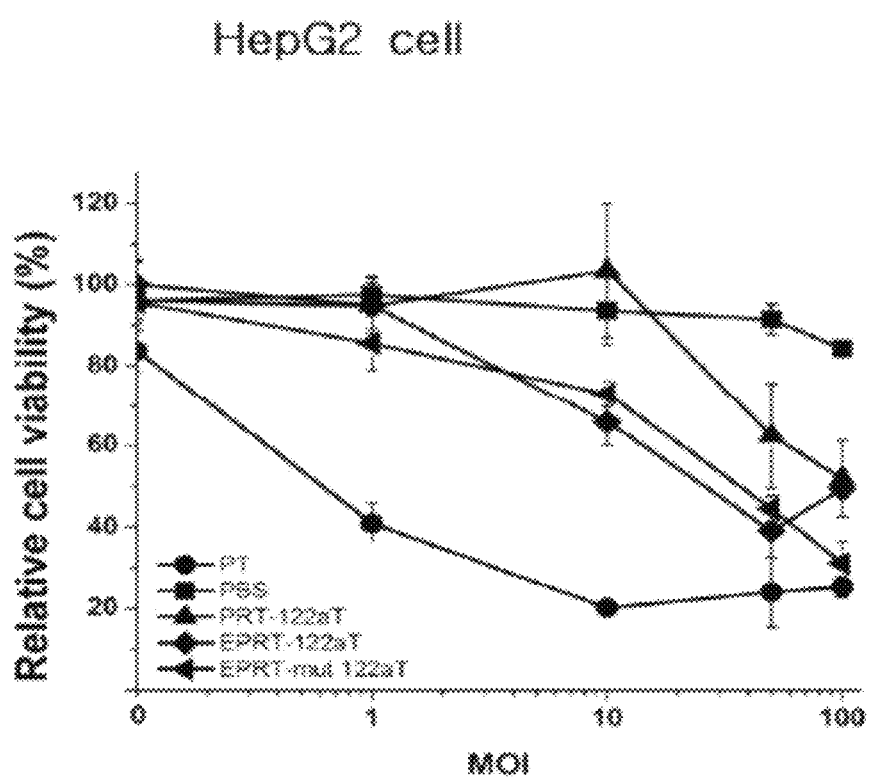
FIGS. 6A and 6B are graphs showing the cell viability observed by MTS assay after transfection of recombinant adenoviruses, Ad-PT, Ad-PRT-122aT, Ad-EPRT-122aT and Ad-EPRT-mut 122aT, into HepG2 (hTERT+, miR122a−) cells and SKLU-1 (hTERT−, miR122a−) cells, respectively, in which it is shown that the induction of cell death was increased in HepG2 cells (FIG. 6A) in which hTERT was expressed, compared to SKLU-1 cells (FIG. 6B) in which hTERT was not expressed.
Figure 6B:
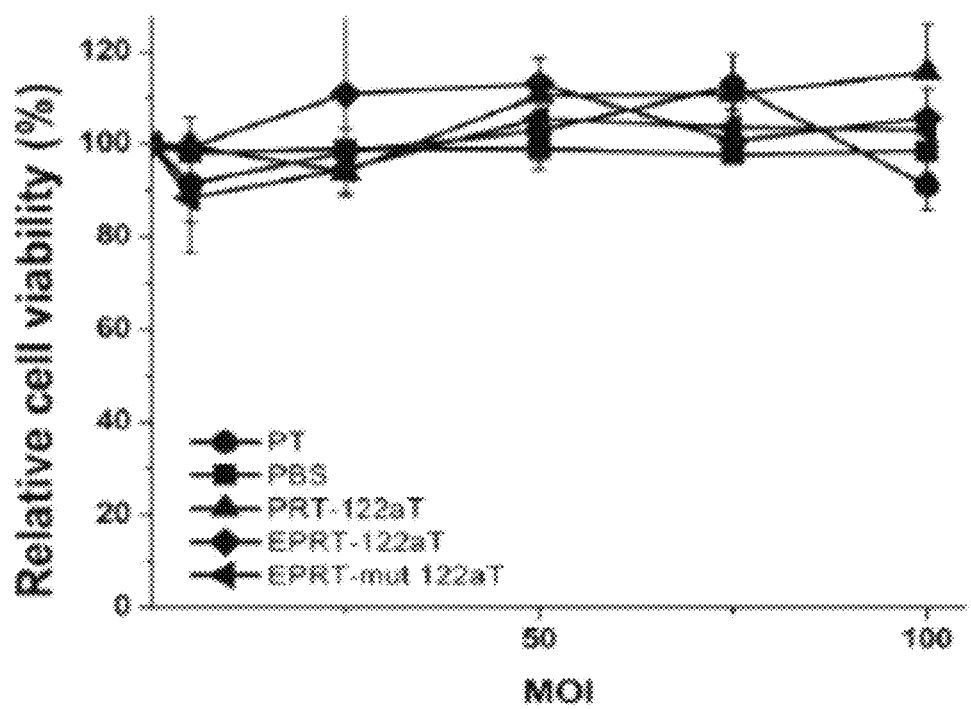

As a result of the experiment, as shown in FIGS. 6A and 6B, it was found that the cell death of HepG2 cells in which hTERT was expressed was increased, compared to SKLU-1 cells in which hTERT was not expressed. From this, it was also found that the ribozyme of the present invention was specific to hepatocellular carcinoma cells in which hTERT was expressed.

Moreover, it could be found that the cell death of HepG2 cells, in which EPRT-122aT and EPRT-mut 122aT expressing the ribozyme to which SD/SA and WPRE were further limited were introduced, was increased, and it could also be found that the therapeutic effect could be increased by the SD/SA sequence and WPRE.

Furthermore, the inventors of the present invention constructed stable cell lines expressing miR-122a in a tetracycline-dependent manner using HepG2 (hTERT−, miR122a−) cells.

Tetracycline-inducible system (Tet-on system) was used to confirm that hTERTrib-TK-miR122aT adenovirus was regulated, TetR and Tet pri-122a regulated by tetracycline were cloned, and stable cell lines were constructed from these clones. Stable cell line expressing TetR was first constructed to inhibit the expression of Tet pri-122a by tetracycline contained in a normal medium. The stable cell line was constructed to inhibit the expression of miR-122a in a normal medium and express miR-122a in a medium further supplemented with tetracycline.

Clone #4 in which the greatest amount of TetR was expressed was selected from seven TetR clones, and then Tet pri-122a stable cell line was constructed to select Tet pri-122a clone #5 in which the expression of miR-122a was turned on/off by tetracycline by Northern blot analysis.

Cells in which miR-122a was expressed by tetracycline and cells in which miR-122a was not expressed due to the absence of tetracycline were transfected with recombinant adenoviruses prepared in Example 2m Ad-PT, Ad-PRT-122aT, Ad-EPRT-122aT, and Ad-EPRT-mut 122aT, respectively.

Figure 7A:
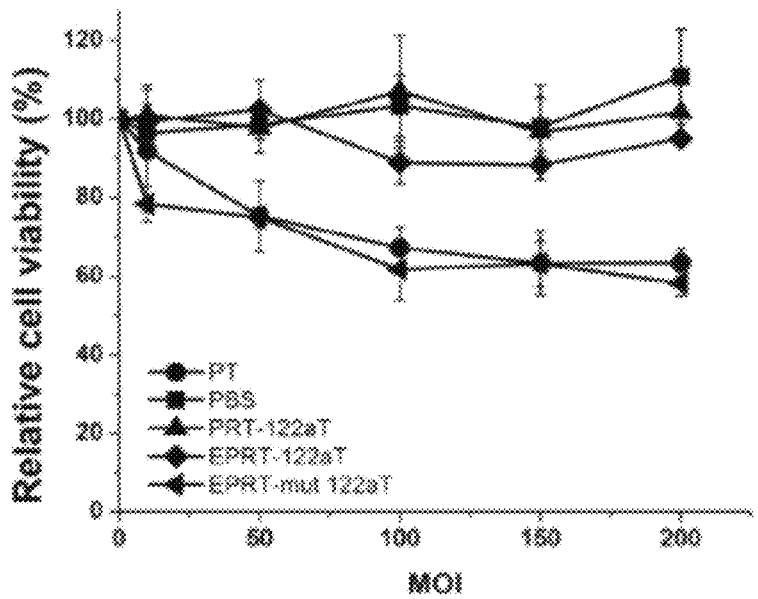
FIGS. 7A and 7B are graphs showing the cell death observed by MTS assay after transfection of recombinant adenoviruses, Ad-PT, Ad-PRT-122aT, Ad-EPRT-122aT, and Ad-EPRT-mut 122aT, into cells in which miR-122a is expressed with the administration of tetracycline and cells in which miR-122a is not expressed without the administration of tetracycline, respectively, in which it is shown that almost no cell death was induced in Tet+ (miR-122a+) cells (FIG. 7A), compared to Tet− (miR-122a−) cells (FIG. 7B).
Figure 7B:
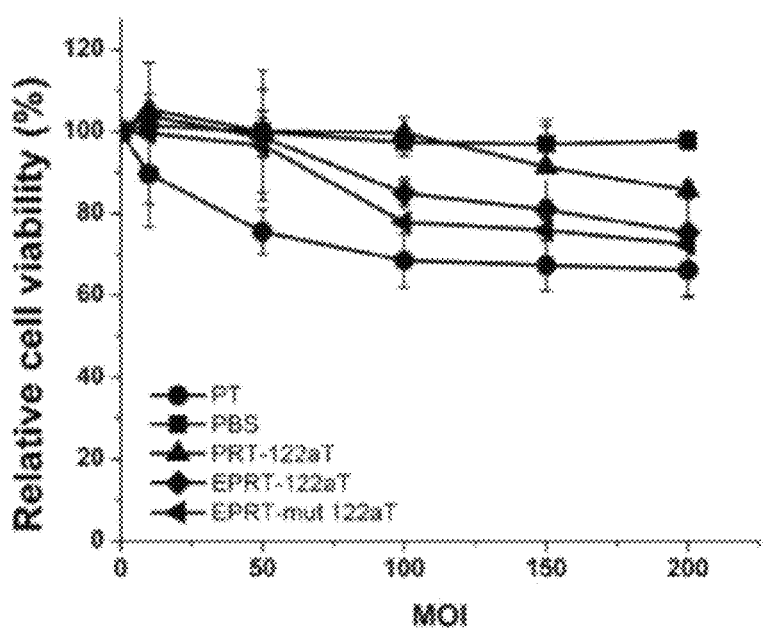

As shown in FIGS. 7A and 7B, it was found that the cell death of Tet+(miR-122a+) cells transfected with Ad-PRT- 122aT and Ad-EPRT-122aT to which miR-122aT was further linked was hardly induced, compared to Tet– (miR-122a–) cells. From this, it was also found that the ribozyme expressed by transduction of the recombinant vector to which miR-122aT was further linked specifically recognized hepatocellular carcinoma cells in which the expression of miR-122 was reduced, resulting in induction of cell death.

Moreover, for the induction of cell death in Tet– (miR-122a–) cells, it could be found that the cell death of cells transfected with Ad-EPRT-122aT expressing the ribozyme to which SD/SA and WPRE were further linked was increased, compared to the cells transfected with Ad-PRT-122aT 5-3. Animal Assay 1) Toxicity Test PBS (negative control), Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$) were injected into 4-5 week-old C57BL mice, respectively. Blood samples were obtained 2 days, 7 days, and 14 days (n=7) after the injection, and ALT and AST levels were measured.

2) Determination of Anticancer Effect

Hep3B cells (hepatocellular carcinoma cells) were implanted into the spleens of 4-5 week-old BALB/c nude mice (Orient Bio Inc.) to construct tumor models (orthotopic multiple hepatocellular carcinoma models). PBS (negative control), Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$) were injected i.v. into the tumor models, respectively. Then, 50 mg/kg of GCV was injected for 10 days for the activation of TK gene. After 10 days, the results were obtained by weighing the tumor tissues and observing the tissues with H&E staining.

Moreover, after systemic treatment of xenograft models (orthotopic multiple hepatocellular carcinoma models), in which tumor was implanted in the spleen, with Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$), respectively, the degree of introduction of adenoviral vectors from the amount of gDNA extracted from normal tissues and hepatocellular carcinoma tissues was determined at the molecular level.

Figure 8:
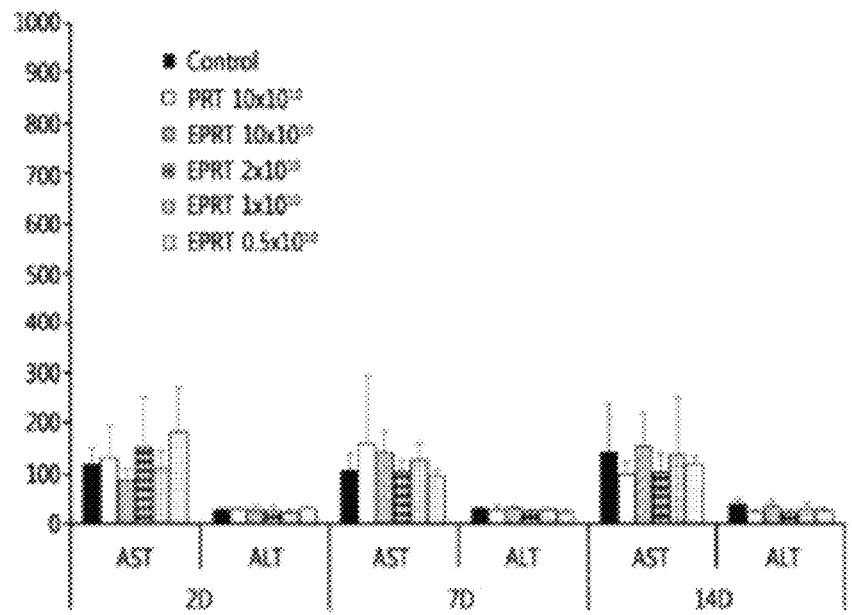
FIG. 8 shows the AST and ALT levels measured over time (at 2 days, 7 days, and 14 days) after treatment with PBS as a negative control, Ad-PRT-122aT ($10 \times 10^{10}$) as a positive control, and adenovirus (Ad-EPRT-122aT) of the present invention at various concentrations in order to examine the toxicity of the adenovirus of the present invention in normal cells due to continuous expression of adenovirus.

As shown in FIG. 8, in order to determine the toxicity to normal cells due to continuous expression of adenovirus, PBS (negative control), Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$) were injected into normal mice without tumor, respectively. Then, GCV was injected for 10 days, and then the shape of the liver and the level of enzymes from the liver were measured.

As a result, for 14 days, the mice injected with Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$) showed changes similar to those of the mice injected with PBS. This suggests that the TK gene is not generated in normal liver. Moreover, it was observed that the AST/ALT levels were similar to those of the mice injected with PBS.

Figure 9A:
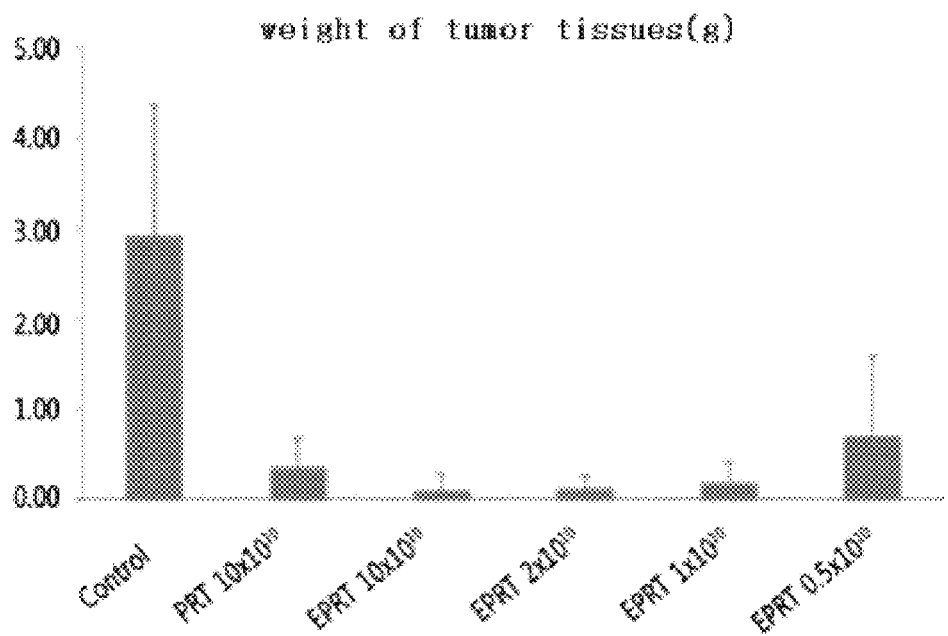
Figure 9B:
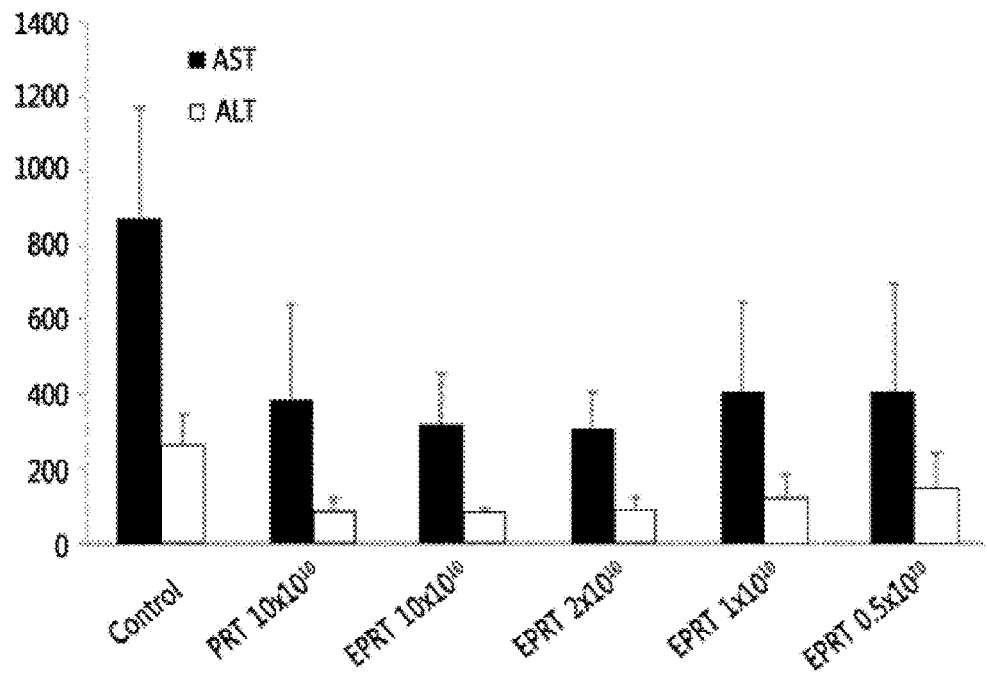

Moreover, as shown in FIGS. 9A and 9B, in order to determine the potential of Ad-EPRT-122aT ribozyme as a therapeutic agent for hepatocellular carcinoma cells, PBS (negative control), Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$) were injected i.v. into tumor models (orthotopic multiple hepatocellular carcinoma models) in which Hep3B cells (hepatocellular carcinoma cells) were implanted into the spleens, and then the results were observed. After injection of viruses, 50 mg/kg of GCV was injected for 10 days for the activation of TK gene. After 10 days, the results were obtained by weighing the tumor tissues. The weight of tumor increased in the negative control injected with PBS, while the weight of tumor was significantly reduced in the mice injected with Ad-PRT-122aT ($10\times10^{10}$), Ad-EPRT-122aT ($10\times10^{10}$), Ad-EPRT-122aT ($2\times10^{10}$), Ad-EPRT-122aT ($1\times10^{10}$), and Ad-EPRT-122aT ($0.5\times10^{10}$). Furthermore, it was found that the treatment with Ad-EPRT-122aT at a concentration of $1\times10^{10}$ had the same results as the treatment at a concentration of $10\times10^{10}$. It was also found that there was no hepatotoxicity due to the treated viruses in the cancer models.

Figure 10:
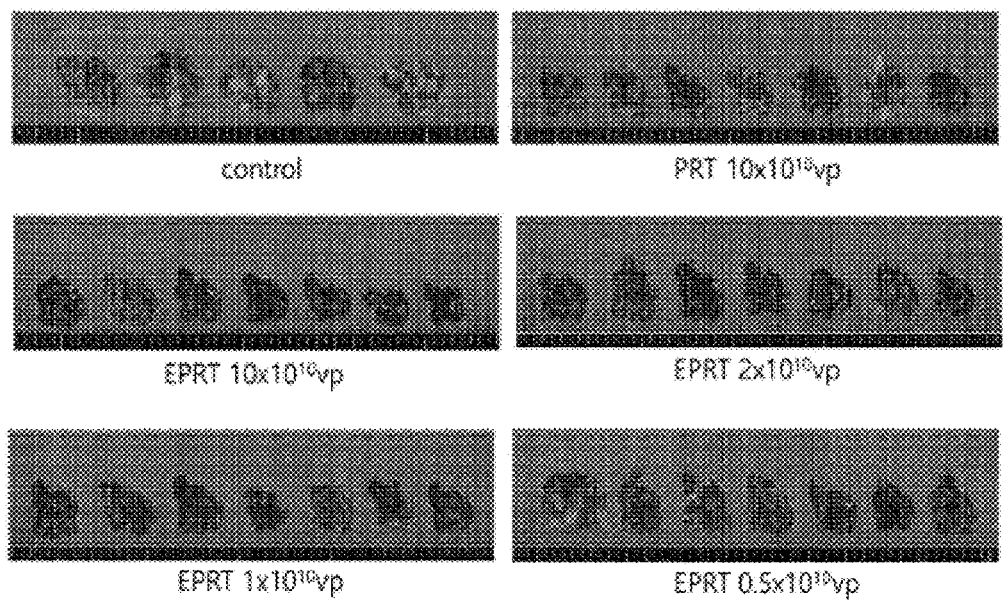
FIG. 10 shows images of mouse livers observed after treatment of orthotopic multiple hepatocellular carcinoma mouse, in which tumor was implanted in the spleen, with PBS as a negative control, Ad-PRT-122aT ($10 \times 10^{10}$) as a positive control, and adenovirus Ad-EPRT-122aT of the present invention, respectively, at various concentrations ($10 \times 10^{10}$, $2 \times 10^{10}$, $1 \times 10^{10}$ and $0.5 \times 10^{10}$).

In addition, as shown in FIG. 10, after the final injection of GCV, the livers of the mice with cancer were observed. Most livers in the control group treated with PBS were replaced with tumor, while the tumor was rarely observed in the mice injected with Ad-PRT-122aT ($10\times10^{10}$), Ad-EPRT-122aT ($10\times10^{10}$), Ad-EPRT-122aT ($2\times10^{10}$), and Ad-EPRT-122aT ($1\times10^{10}$), and the tumor was partially observed in the mice injected with Ad-EPRT-122aT ($0.5\times10^{10}$). Only very small tumors could be observed under a microscope. This suggests the Ad-EPRT-122aT shows an equivalent cancer therapeutic efficacy through the introduction of adenovirus at a concentration of $\frac{1}{10}$ of Ad-PRT-122aT ($10\times10^{10}$). Besides, FIG. 11 shows the results of H&E staining that neither damage to liver tissues and nor immune response occurred in the liver tissues.

Moreover, as shown in FIG. 12, it was observed that both normal liver tissues and implanted hepatocellular carcinoma tissues were transfected with Ad-EPRT-122aT in a dose-dependent manner. This result suggests that the systemic treatment of hepatocellular carcinoma animal models with hTERT targeting ribozyme derivative adenovirus (Ad-EPRT-122aT) into which SD/SA, WPRE, and miR-T are introduced exhibits an equivalent anticancer efficacy without hepatotoxicity, even with a small amount, that is $\frac{1}{10}$ of that of the existing ribozyme adenovirus. That is, it was found that the anticancer efficiency was increased by the ribozyme into which SD/SA and WPRE were introduced even in animal models. Therefore, the results show the introduction of adenovirus into normal liver tissues and implanted hepatocellular carcinoma tissues in animal models determined at the molecular level.

From these results, it could be found that when SD/SA and WPRE are further linked to a trans-splicing ribozyme to which a cancer gene therapeutic agent is linked, the expression of ribozyme increases, which in turn increases the induction of cell death, and the linkage of miR-122aT targeting miR-122a does not induce the cell death of normal liver cells in which the expression of miR-122a normally occurs, but induces the cell death of hepatocellular carcinoma cells in which the expression of miR-122a is reduced, allowing hepatocellular carcinoma cell-specific treatment.

Therefore, it is possible to further increase the cancer-specific therapeutic effect by increasing the induction of cell death of hepatocellular carcinoma cells and inhibiting the cell death is of normal cells to minimize side effects using the trans-splicing ribozyme of the present invention to which SD/SA, WPRE, and miR-122aT are further linked, and to which a cancer gene therapeutic agent is linked.

From the foregoing description, it will be appreciated by those skilled in the art that the present invention can be embodied in other specific forms without departing from the spirit or essential characteristics thereof. In this regard, the above-described embodiments are considered in all respects to be illustrative and not restricted. The scope of the invention is indicated by the appended claims rather than the foregoing description and all changes that come within the meaning and range and equivalence thereof are intended to be embraced therein.

The invention claimed is:

1. A recombinant vector comprising:
   (i) a phosphoenolpyruvate carboxykinase (PEPCK) promoter as a liver cell-specific promoter comprising a nucleic acid sequence of SEQ ID NO: 2; and
   (ii) a ribozyme-target gene expression cassette comprising a telomerase reverse transcriptase (TERT) mRNA as a trans-splicing ribozyme targeting a cancer-specific gene and a herpes simplex virus-thymidine kinase (HSVtk) gene as a target gene linked to the 3' exon of the ribozyme,
   wherein a splicing donor/splicing acceptor sequence (SD/SA sequence) is linked to the 5' end of the ribozyme-target gene expression cassette and a woodchuck hepatitis virus posttranscriptional regulatory element (WPRE) is linked to the 3' end of the ribozyme-target gene expression cassette, and
   wherein (iii) a nucleic acid sequence that binds complementarily to a micro RNA-122a (microRNA-122a, miR-122a) is further linked to the 3' end of the WPRE.

2. The recombinant vector of claim 1, wherein the trans-splicing ribozyme comprises a nucleic acid sequence of SEQ ID NO: 5.

3. The recombinant vector of claim 1, wherein the HSVtk gene comprises a nucleic acid sequence of SEQ ID NO: 6.

4. A transformed cell into which the recombinant vector of claim 1 is introduced.

5. A ribozyme expressed from the recombinant vector of claim 1.

6. A pharmaceutical composition for preventing or treating hepatocellular carcinoma, comprising the recombinant vector of claim 1 as an active ingredient.

7. A method for treating hepatocellular carcinoma, comprising administering to a subject in need thereof a pharmaceutically effective amount of the recombinant vector of claim 1.

8. A pharmaceutical composition for preventing or treating hepatocellular carcinoma, comprising the ribozyme of claim 5 as an active ingredient.

9. A method for treating hepatocellular carcinoma, comprising administering to a subject in need thereof a pharmaceutically effective amount of the ribozyme of claim 5.

* * * * *